(12) United States Patent
Marzio et al.

(10) Patent No.: US 7,504,248 B2
(45) Date of Patent: Mar. 17, 2009

(54) PRODUCTION OF VIRUSES VIRAL ISOLATES AND VACCINES

(75) Inventors: Giuseppe Marzio, Amsterdam (NL); Maria Grazia Pau, Leiden (NL); Dirk Jan Elbertus Opstelten, Oegstgeest (NL); Alphonsus Gerardus Cornelis Maria Uytdehaag, Vleuten (NL)

(73) Assignee: Crucell Holland B.V., Leiden (NL)

( * ) Notice: Subject to any disclaimer, the term of this patent is extended or adjusted under 35 U.S.C. 154(b) by 471 days.

(21) Appl. No.: 10/497,832

(22) PCT Filed: Dec. 9, 2002

(86) PCT No.: PCT/NL02/00804

§ 371 (c)(1),
(2), (4) Date: Jan. 10, 2005

(87) PCT Pub. No.: WO03/048348

PCT Pub. Date: Jun. 12, 2003

(65) Prior Publication Data

US 2005/0123564 A1    Jun. 9, 2005

(30) Foreign Application Priority Data

Dec. 7, 2001  (WO) ................... PCT/NL01/00892
Jan. 25, 2002  (EP) ................... 02075327

(51) Int. Cl.
*C12N 7/00*  (2006.01)
(52) U.S. Cl. .................................. 435/235.1
(58) Field of Classification Search ............... 435/235.1
See application file for complete search history.

(56) References Cited

U.S. PATENT DOCUMENTS

| | | | |
|---|---|---|---|
| 4,703,008 A | 10/1987 | Lin | |
| 4,835,260 A | 5/1989 | Shoemaker | |
| 5,047,335 A | 9/1991 | Paulson et al. | |
| 5,192,539 A | 3/1993 | Van Der Marel et al. | |
| 5,441,868 A | 8/1995 | Lin | |
| 5,457,089 A | 10/1995 | Fibi et al. | |
| 5,494,790 A | 2/1996 | Sasaki et al. | |
| 5,631,158 A | 5/1997 | Dorai et al. | |
| 5,767,078 A | 6/1998 | Johnson et al. | |
| 5,773,569 A | 6/1998 | Wrighton et al. | |
| 5,789,247 A | 8/1998 | Ballay et al. | |
| 5,830,851 A | 11/1998 | Wrighton et al. | |
| 5,835,382 A | 11/1998 | Wilson et al. | |
| 5,856,298 A | 1/1999 | Strickland | |
| 5,994,128 A | 11/1999 | Fallaux et al. | |
| 6,033,908 A | 3/2000 | Bout et al. | |
| 6,475,753 B1 | 11/2002 | Ruben et al. | |
| 6,492,169 B1 | 12/2002 | Vogels et al. | |
| 6,558,948 B1 | 5/2003 | Kochanek et al. | |
| 6,653,101 B1 | 11/2003 | Cockett et al. | |
| 6,855,544 B1 | 2/2005 | Hateboer et al. | |
| 6,878,549 B1 | 4/2005 | Vogels et al. | |
| 2002/0116723 A1 | 8/2002 | Grigliatti et al. | |
| 2003/0087437 A1 | 5/2003 | Asada et al. | |
| 2003/0092160 A1 | 5/2003 | Bout et al. | |

FOREIGN PATENT DOCUMENTS

| | | |
|---|---|---|
| EP | 0 185 573 | 6/1986 |
| EP | 0 411 678 | 2/1991 |
| EP | 0 833 934 B1 | 4/1998 |
| WO | WO 93/03163 | 2/1993 |
| WO | WO 95/05465 | 2/1995 |
| WO | WO 95/29994 | 11/1995 |
| WO | WO 97/00326 | 1/1997 |
| WO | WO 98/18926 | 5/1998 |
| WO | WO 98/39411 | 9/1998 |
| WO | WO 98/44141 | 10/1998 |
| WO | WO 99/05268 | 2/1999 |
| WO | WO 99/24068 | 5/1999 |
| WO | WO 00/61164 | 10/2000 |
| WO | WO 00/63403 | 10/2000 |
| WO | WO 01/38362 A2 | 5/2001 |
| WO | WO 02/053580 | 7/2002 |
| WO | WO 03/038100 A1 | 5/2003 |
| WO | WO 03/048197 A1 | 6/2003 |
| WO | WO 03/048348 A2 | 6/2003 |
| WO | WO 03/051927 | 6/2003 |
| WO | WO 2004/003176 | 1/2004 |
| WO | WO 2004/099396 | 11/2004 |

OTHER PUBLICATIONS

Pau et al. (Vaccine 2001 vol. 19 pp. 2716-2721).*

(Continued)

*Primary Examiner*—Bruce Campell
*Assistant Examiner*—Myron G Hill
(74) *Attorney, Agent, or Firm*—TraskBritt

(57) ABSTRACT

The present invention discloses methods for producing and/or propagating virus particles, such as influenza virus particles, that are present in a virus isolate obtained from an infected subject by contacting a host cell with a virus particle and culturing the cell under conditions conducive to propagation of the virus particle. The invention also provides a method for selective propagation of a set of virus particles, such as influenza virus particles present in an influenza isolate, which have an affinity for receptors comprising a specific glycosylation residue.

11 Claims, 10 Drawing Sheets

OTHER PUBLICATIONS

Ghosh-Choudhury et al., Protein IX, a minor component of the human adenovirus capsid, is essential for the packaging of the full length genomes, The EMBO Journal, 1987, pp. 1733-1739, vol. 6, No. 6.

Louis et al., Cloning and Sequencing of the Cellular—Viral Junctions from the Human Adenovirus Type 5 Transformed 293 Cell Line, Virology, 1997, pp. 423-429, vol. 233.

Setoguchi et al., "Stimulation of Erythropoiesis by in vivo gene therapy: Physiologic consequences of transfer of the humanerythropoietin gene to experimental animals using an adenovirus vector," Blood, Nov. 1, 1994, pp. 2946-2953, vol. 84, No. 9.

European Search Report 05 10 0732, Apr. 7, 2005.

Fallaux et al, "New helper cells and matched early region 1-deleted adenovirus vectors prevent generation of replication-competent adenoviruses," Human Gene Therapy, Sep. 1, 1998, vol. 9, No. 1, pp. 1909-1917. Abstract.

Grand et al., "Modulation of the level of expression of cellular genes in adenovirus 12-infected and transformed human cells," Eur Mol Biol Organ J. 1986, 5 (6) 1253-160. Abstract.

Grand et al., "The high levels of p53 present in adenovirus early region 1-transformed human cells do not cause up-regulation of MDM2 expression," Virology, 1995, vol. 210, No. 2, pp. 323-334. Abstract.

Yu et al., "Enhanced c-erbB-2/neu expression in human ovarian cancer cells correlates with more severe malignancy that can be suppressed by E1A," Cancer Res., 1993, 53 (4) 891-8. Abstract.

Bout et al., "Production of RCA-free batches of E1-deleted recombinant adenoviral vectors on PER.C6," Nucleic Acids Symp. Ser. 1998, XP-002115716, pp. 35-36.

Boutl et al., A novel packaging cell line (PER.C6) for efficient production of RCA-free batches of E1-deleted recombinant adenoviral vectors, Cancer Gene Therapy, 1997, pp. S32-S33, vol. 4, No. 6.

Bout et al., "Improved helper cells for RCA-free production of E1-deleted recombinant adenovirus vectors," Cancer Gene Therapy, 1996, pp. S24, vol. 3, No. 6.

Schiedner et al., Abstract, Efficient transformation of primary human amniocytes by E1 functions of Ad5: generation of new cell lines for adenoviral vector production, 2000, Hum. Gene Ther. 11, 2105-2116.

Pazur et al., Abstract, Oligosaccharides as immunodeterminants of erythropoietin for two sets of anti-carbohydrate antibodies, Journal of Protein Chemistry, Nov. 2000, pp. 631-635, vol. 19, No. 8.

Cronan, Abstract, Biotination of Proteins in-vivo a post-translational modification to label purify and study proteins, Journal of Biological Chemistry, Jun. 25, 1990, pp. 10327-10333, vol. 265, No. 18.

Stockwell et al., High-throughput screening of small molecules in Miniaturized Mammalian Cell-based Assays involving Post-translational Modifications, Chemistry and Biology, Feb. 1999, pp. 71-83, vol. 6, No. 2.

Pacitti et al., Inhibition of Reovirus Type 3 Binding to Host Cells by Sialylated Glycoproteins Is Mediated through the Viral Attachment Protein, Journal of Virology, May 1987, pp. 1407-1415, vol. 61, No. 5, American Society for Microbiology.

Zhang et al., Stable expression of human alpha-2,6-sialytransferase in Chinese hamster ovary cells: functional consequences for human erythropoietin expression and bioactivity, BBA—General Subjects, 1998, pp. 441-452, vol. 1425, No. 3, Elsevier Science Publishers, NL.

Grabenhorst et al., Construction of stable BHK-21 cells coexpressing human secretory glycoproteins and human Gal(beta-1-4)GlcNAc-R alpha-2,6-sialyltransferase alpha-2,6-Linked NeuAc is preferentially attached to the Gal(beta-1-4)GlcNAc(beta-1-2)Man(alpha-1-3)-branch of diantennary oligosaccharides from secreted recombinant beta-trace protein, Eur. J. Biochem, 1995, pp. 718-725, vol. 232, No. 3, Berlin, Germany.

Hollister et al., Stable expression of mammalian beta 1,4-galactosyltransferase extends the N-glycosylation pathway in insect cells, Glycobiology, 1998, pp. 473-480, vol. 8, No. 5, IRL Press, United Kingdom.

Jenkins et al., Getting the glycosylation right: Implications for the biotechnology industry, Nature Biotechnology, Aug. 1996, pp. 975-981, vol. 14, No. 8, Nature Publishing, US.

Weikert et al., Engineering Chinese hamster ovary cells to maximize sialic acid content of recombinant glycoproteins, Nature Biotechnology, Nov. 1999, pp. 1116-1121, vol. 17, No. 11, Nature Pub. Co., New York, NY, US.

Minch et al., Tissue Plasminogen Activator Coexpressed in Chinese Hamster Ovary Cells with alpha(2,6)-Sialytransferase Contains NeuAc-alpha(2,6)Gal-beta(1,4)Glc-N-AcR Linkages, Biotechnol. Prog., 1995, pp. 348-351, vol. 11, No. 3.

Alkhatib et al., "Expression of Bicistronic Measles Virus P/C mRNA by Using Hybrid Adenovirus: Levels of C Protein Synthesized In Vivo Are Unaffected by the Presence or Absence of the Upstream P Initiator Codon," Journal of Virology, Nov. 1988, pp. 4059-4068, vol. 62, No. 11.

Alkhatib et al., "High-Level Eurcaryotic In Vivo Expression of Biologically Active Measles Virus Hemagglutinin by Using an Adenovirus Type 5 Helper-Free Vector System," Journal of Virology, Aug. 1988, pp. 2718-2727, vol. 62, No. 8.

Berg et al., High-Level Expression of Secreted Proteins from Cells Adapted to Serum-Free Suspension Culture, Research Report, BioTechniques, 1993, pp. 972-978, vol. 14, No. 6.

Brown et al., "Evaluation of Cell Line 293 for Virus isolation in Routine Viral Diagnosis," Journal of Clinical Microbiology, Apr. 1986, pp. 704-708, vol. 23, No. 4.

Bukreyev et al., "Recombinant Respiratory Syncytial Virus from Which the Entire SH Gene Has Been Deleted Grows Efficiently in Cell Culture and Exhibits Site-Specific Attenuation in the Respiratory Tract of the Mouse," Journal of Virology, Dec. 1997, pp. 8973-8982, vol. 71, No. 12.

Caravokyri et al., "Constitutive Episomal Expression of Polypeptide IX (pIX) in a 293-Based Cell Line Complements that Deficiency of pIX Mutant Adenovirus Type 5," Journal of Virology, Nov. 1995, pp. 6627-6633, vol. 69, No. 11.

Certificate of deposit of the PER.C6 cell line (ECACC deposit under No. 96022940), 1996.

Ciccarone et al., "Lipofectamine 2000 Reagent for Transfection of Eukaryotic Cells," Focus, 1999, pp. 54-55, vol. 21, No. 2.

Cote et al., Serum-Free Production of Recombinant Proteins and Adenoviral Vectors by 293SF-3F6 Cells, Biotechnology and Bioengineering, Sep. 5, 1998, pp. 567-575, vol. 59, No. 5.

DuBridge et al., "Analysis of Mutation in Human Cells by Using an Epstein-Barr Virus Shuttle System," Molecular and Cellular Biology, Jan. 1987, pp. 397-387, vol. 7, No. 1.

Endo et al., Growth of Influenza A Virus in Primary, Differentiated Epithelial Cells Derived from Adenoids, Journal of Virology, Mar. 1996, pp. 2055-2058, vol. 70, No. 3.

Fallaux et al., Characterization of 911: A New Helper Cell Line for the Titration and Propagation of Early Region 1-Deleted Adenoviral Vectors, Human Gene Therapy, Jan. 20, 1996, pp. 215-222, vol. 7.

Gallimore et al., Transformation of Human Embryo Retinoblasts with Simian Virus 40, Adenovirus and ras Oncogenes, Anticancer Research, 1986, pp. 499-508, vol. 6.

Garnier et al., Scale-up of the adenovirus expression system for the production of recombinant protein in human 293S cells, Cytotechnology, 1994, pp. 145-155, vol. 15.

Graham et al., "Characteristics of a Human Cell Line Transformed by DNA from Human Adenovirus Type 5," J. Gen. Virol., 1997, pp. 59-72, vol. 36.

Graham et al., "Growth of 293 cells in suspension culture." J Gen Virol, Mar. 1987, pp. 937-940, vol. 68.

Holzer et al., "Construction of a Vaccinia Virus Deficient in the Essential DNA Repair Enzyme Uracil DNA Glycosylase by a Complementing Cell Line," Journal of Virology, Jul. 1997, pp. 4997-5002, vol. 71, No. 7.

Inoue et al., Production of Recombinant Human Monoclonal Antibody Using ras-Amplified BHK-21 Cells in a Protein-free Medium, Biosci. Biotech. Biochem, 1996, pp. 811-817, vol. 60, No. 5.

Interlocutory Decision of the Opposition Division of Jul. 21, 2003 in the case EP 0 695 351(European application 94 913 174.2).

Lopez et al., Efficient production of biologically active human recombinant proteins in human lymphoblastoid cells form integrative and episomal expression vectors, Gene, 1994, pp. 285-291, vol. 148.

Lutz et al., "The Product of the Adenovirus Intermediate Gene IX Is a Transcriptional Activator," Journal of Virology, Jul. 1997, pp. 5102-5109, vol. 71, No. 7.

Manservigi et al., "Protection from Herpes Simplex Virus Type 1 Lethal and Latent Infections by Secreted Recombinant Glycoprotein B Constitutively Expressed in Human Cells with a BK Virus Episomal Vector," Journal of Virology, Jan. 1990, pp. 431-436, vol. 64, No. 1.

Massie et al., Improved Adenovirus Vector Provides Herpes Simplex Virus Ribonucleotide Reductase R1 and R2 Subunits Very Efficiently, Biotechnology, Jun. 1995, pp. 602-608, vol. 13.

Merten et al., Production of Influenza Virus in Cell Cultures for Vaccine Preparation, Exp Med Biol., 1996, pp. 141-151, vol. 397.

Neumann et al., "Generation of influenza A viruses entirely from cloned cDNAs," Proc. Natl. Acad. Sci., Aug. 1999, pp. 9345-9350, vol. 96.

Notice of Opposition to a European Patent for 1 161 548 by Serono, 2005.

Opposition against European patent 1 108 878 B1 filed Oct. 5, 2005 in the name and on behalf of CEVEC Pharmaceuticals GmbH.

Opposition against European patent 1 161 548 B1 filed Nov. 16, 2005, in the name and on behalf of CEVEC Pharmaceutical GmbH.

Opposition against European patent 1108787 filed Oct. 5, 2005 in the name and on behalf of Probiogen AG.

Ory et al., "A stable human-derived packaging cell line for production of high titer retrovirus/vesicular stomatitis virus G pseudotypes," Proc. Natl. Acad. Sci., Oct. 1996, pp. 11400-11406, vol. 93.

Parkinson et al., "Stable Expression of a Secretable Deletion Mutant of Recombinant Human Thrombomodulin in Mammalian Cells," The Journal of Biological Chemistry, Jul. 25, 1990, pp. 12602-12610, vol. 265, No. 21.

Paul et al., Increased Viral Titer Through Concentration of Viral Harvests from Retroviral Packaging Lines, Human Gene Therapy, 1993, pp. 609-615, vol. 4.

Pleschka et al., "A Plasmid-Based Reverse Genetics System for Influenza A Virus," Journal of Virology, Jun. 1996, pp. 4188-4192, vol. 70, No. 6.

PubMed listing of abstracts (visited Apr. 10, 2005) <http://www.ncbi.nlm.nih.gov/entrez/query.fcgi?CMD=search&DB=pubmed.

Reina et al., Comparison of Madin-Darby Canine Kidney cells (MDCK) with a Green Monkey Continuous Cell Line (Vero) and Human Lung Embryonated Cells (MRC-5) in the Isolation of Influenza A Virus from Nasopharyngeal Aspirates by Shell Vial Culture, Journal of Clinical Microbiology, Jul. 1997, pp. 1900-1901, vol. 35, No. 7.

Rhim et al., "Development of Human Cell Lines from Multiple Organs," Annals of the New York Academy of Sciences, 2000, pp. 16-25, vol. 919.

Spector et al., "Regulation of Integrated Adenovirus Sequences During Adenovirus Infection of Transformed Cells," Journal of Virology, Dec. 1980, pp. 860-871, vol. 36, No. 3.

Stevens et al., "The N-Terminal Extension of the Influenza B Virus Nucleoprotein Is Not Required for Nuclear Accumulation or the Expression and Replication of a Model RNA," Journal of Virology, Jun. 1998, pp. 5307-5312, vol. 72, No. 6.

U.S. Department of Health and Human Services, Public Health Service, Food and drug Administration, Center for Biologics Evaluation and Research, International Association for Biologicals, National Institute of Allergy and Infectious Diseases, National Vaccine Program Office, World Health Organization, Evolving Scientific and Regulatory Perspectives on Cell Substrates for Vaccine Development, Workshop, Friday, Sep. 10, 1999 (visited Sep. 30, 2005) <http://www.fda.gov.cber.minutes/0910evolv.txt>.

Yan et al., Novel Asn-linked oligosaccharides terminating in GalNAcbeta(1-4)[Fucalpha(1-3)]GlcNAcbeta(1-.) are present in recombinant human Protein C expressed in human kidney 293 cells, Glycobiology, 1993, pp. 597-608, vol. 3, No. 6.

Yeager et al., Constructing immortalized human cell lines, Current Opinion Biotechnology, 1999, pp. 465-469, vol. 10.

Yeh et al., Adenoviral Vectors, pp. 25-42 of "Concepts in Gene Therapy," Publisher: Walter de Gruyter, New York.

Yasuo Suzuki, Gangliosides as influenza virus receptors. Variation of influenza viruses and their recognition of the receptor sialo-sugar chains, Progress in Lipid Research, 1994, pp. 429-457, vol. 33, No. 4, Pergamon Press, Paris, France.

Yallop et al., "PER.C6® Cells for the Manufacture of Biopharmaceutical Proteins," Modern Biopharmaceuticals, Ed. J. Knablein, 2005, WILEY-VCH Verlag GmbH & Co. KGaA, Weinheim, Germany.

Pau et al., Abstract, The human cell line PER.C6 provides a new manufacturing system for the production of influenza vaccines, Vaccine, Mar. 21, 2001, pp. 2716-2721, vol. 19, No. 17-19.

Carroll et al., Abstract, Differential Infection of Receptor-modified Host Cells by Receptor-Specific Influenza Viruses, Virus Research, Sep. 1985, pp. 165-179, vol. 3, No. 2.

PCT International Search Report, PCT/NL02/00804, dated Sep. 26, 2003.

* cited by examiner

PRODUCTION OF VIRUSES VIRAL ISOLATES AND VACCINES

CROSS-REFERENCE TO RELATED APPLICATIONS

This application is a national entry under 35 U.S.C. § 371 from PCT International Application No. PCT/NL02/00804, filed on Dec. 9, 2002, 1996, published in English as international publication WO 03/048348 A2 on Jun. 12, 2003, which claims the benefit of PCT/NL01/00892, filed Dec. 7, 2001 and EP02075327.2, filed Jan. 25, 2002, the entirety of which is incorporated by reference.

SEQUENCE LISTING

A sequence listing has been included herein to comply with the requirements of 37 C.F.R. §§ 1.821 through 1.825.

TECHNICAL FIELD

The invention relates to the field of medicine. The invention further relates to vaccines providing protection against influenza infection and to methods and means of obtaining these.

BACKGROUND

Influenza viruses are the etiological agents of flu, a highly contagious respiratory illness that has afflicted humans since ancient times. The virus was first identified in 1933, but numerous epidemics almost certainly attributable to influenza were reported throughout the centuries (Potter 1998). There have been three major cases of outbreaks of influenza in the last century. The so-called "Spanish flu" of 1918 was particularly severe. It resulted in the death of an estimated 20 to 40 million people worldwide, the most severe recorded outbreak of human disease known in history. In 1957 the "Asian flu" killed an estimated 1 million people, and in 1968 the "Hong Kong flu" was lethal for more than 700,000 individuals. In spite of the efforts of the scientific community, infections caused by influenza viruses continue to claim each year a heavy toll in terms of cases of illness and death as well as economic consequences. Recent work has helped to explain the unusual virulence of some influenza strains that caused major pandemics in the past (Gibbs et al. 2001; Hatta et al. 2001). However, the understanding of the underlying pathogenic mechanisms is incomplete, thus limiting efficient prevention and treatment of the disease.

According to estimates that include all age groups, in the U.S. alone 48 million persons suffer from flu each year. These epidemics result in approximately 20,000 deaths per year on top of about 4 million individuals that need treatment in a hospital (CDC statistics). Infants, children and the elderly are particularly susceptible to influenza infection. However, the appearance of a new virus variant with high pathogenic and infective capacity remains a major threat to all individuals. This was proven to be the case in 1997, when a virus identified in Hong Kong caused the death of one third of the 18 clinically diagnosed cases (Claas et al. 1998; Subbarao et al. 1998).

Birds represent the major reservoir of influenza virus. In particular, all known subtypes of influenza A virus (together with subtype B the most common cause of flu in humans) have been isolated from wild—as well as domestic birds. However, an avian influenza A virus normally is not directly transmitted from birds to humans. In this respect, the only exception so far recorded has been the 1997 Hong Kong virus mentioned above. Several viral proteins are thought to play a role in conferring host specificity, but the most important factor is the hemagglutinin (HA) membrane protein.

The HA gene was one of the first genes of the influenza virus to be identified and sequenced. It codes for a transmembrane protein directly involved in attachment to and penetration into the host cell. HA initiates infection by binding to terminal sialyl-oligosaccharide receptor determinants present on glycoproteins and gangliosides present on the host cell surface. Terminal sialic acid residues of natural sialyl-glycoproteins and gangliosides are known to be the minimum determinants of binding. However, binding depends also on the type of sialic acid linkage to penultimate galactose and on the structure of more distant parts of the sialyl-glycoconjugate.

Human influenza viruses bind preferentially to receptors containing the sialic acid alpha-2,6-galactose (SAalpha2,6Gal) linkage, whereas avian viruses use the SAalpha2,3Gal linkage (reviewed in Suzuki 1994). This binding specificity determines also the cell tropism of the virus inside the host. Human influenza virus infection (and replication) are restricted to the respiratory tract, whereas avian influenza virus is found mainly in the cells lining the intestinal tract as well as in the lungs of birds. Using sialic acid-galactose linkage specific lectins, it was shown that residues of sialic acid linked to galactose by the alpha-2,6 linkage but not SAalpha2,3Gal are present on the surfaces of epithelial cells of the human trachea (Baum and Paulson 1990). Furthermore, also the abundance of SAalpha2,3Gal moieties in respiratory mucins contributes to maintain the SAalpha2,6Gal-specific phenotype of human influenza of HA (Baum and Paulson 1990; Couceiro et al. 1993).

In most laboratories propagation of primary isolates is still carried out in the chorio-allantoic sac of embryonated chicken eggs. This is due not only to historical reasons, but also to the lack of an appropriate alternative growth medium. This is currently also the system of choice for the production of large amounts of virus to be used in vaccine preparations. However, embryonated eggs have serious limitations as a host system for vaccine production. For instance, the lack of reliable year-round supplies of high-quality eggs as well as the limited availability of embryonated eggs in general may hamper vaccine production in case of the sudden outbreak of a new influenza subtype. Other disadvantages of this production system are the lack of flexibility, the risk of the presence of toxins and the risks of adventitious viruses, particularly retroviruses, and concerns about sterility.

Besides these limitations, culturing the virus on eggs poses a very significant additional problem, which is particularly important for vaccine purposes. There is now ample evidence that egg cultures lead to substrate-specific adaptation of the virus. In fact, even few passages in the allantoic sac of eggs are sufficient for a primary human isolate to adapt to the SAalpha2,3Gal binding phenotype (Rogers et al. 1985). This is due to the presence of SA-alpha2,3Gal but not SAalpha2,6Gal residues on the cells lining the surface of the chicken embryo choric-allantoic membrane. Virus variants present in primary isolates that are able to specifically interact with SAalpha2,3Gal residues have a replicative advantage over virus variants that interact more specifically to SAalpha2,6Gal residues. The SAalpha2,3Gal-specific virus variants are thus selected for in embryonated eggs (Gambaryan et al. 1999; Gambaryan at al. 1997). Egg-adaptation not only increases the affinity for SAalpha2,3Gal, but it also results in decreased affinity for SAalpha2,6Gal. HA, in fact, cannot accommodate both types of analogues equally well, and multiple mutations have been identified that confer this altered binding specificity (Daniels et al. 1987; Gambaryan et al. 1999; Ito et al. 1997; Suzuki et al. 1989). Given the importance of HA in eliciting a specific immune response, these mutations result in major alterations of its antigenic properties (Ilobi et al. 1994; Robertson et al. 1994). Consequently, immunization with vaccines containing HA molecules bearing egg-induced mutations induces less neutralizing antibody to wild-type influenza strains at the expenses of the level of protection achieved (Newman et al. 1993).

SUMMARY OF THE INVENTION

The present invention discloses methods for producing and/or propagating virus particles such as influenza virus particles that preferably are present in a virus isolate obtained from an infected subject, said method comprising the steps of: contacting a cell with a virus particle and culturing said cell under conditions conducive to propagation of said virus particle, wherein said cell over-expresses a nucleic acid encoding an alpha2,6 or an alpha2,3 sialyltransferase. The invention also provides a method for selective propagation of a set of virus particles such as influenza virus particles present in an influenza isolate, wherein said set of virus particles has affinity for receptors comprising a specific glycosylation residue, said method comprising the steps of: incubating a cell with said isolate; culturing said cell under conditions conducive to propagation of said virus particle; and harvesting virus particles so produced from said cell and/or said culture medium.

The invention further provides novel vaccines and methods for making such vaccines, wherein said methods preferably comprise the steps of: treating the produced virus particles to yield antigenic parts; and harvesting at least one antigenic part such as hemagglutinin and/or neuraminidase from influenza virus. The invention further provides cells and cell lines and the use thereof, that over-express certain proteins involved in glycosylation for the production of vaccines, e.g., vaccines against influenza infection. Cells of the present invention are preferably human and transformed by adenovirus E1, such as PER.C6 cells or derivatives thereof.

DETAILED DESCRIPTION

Figure 1:
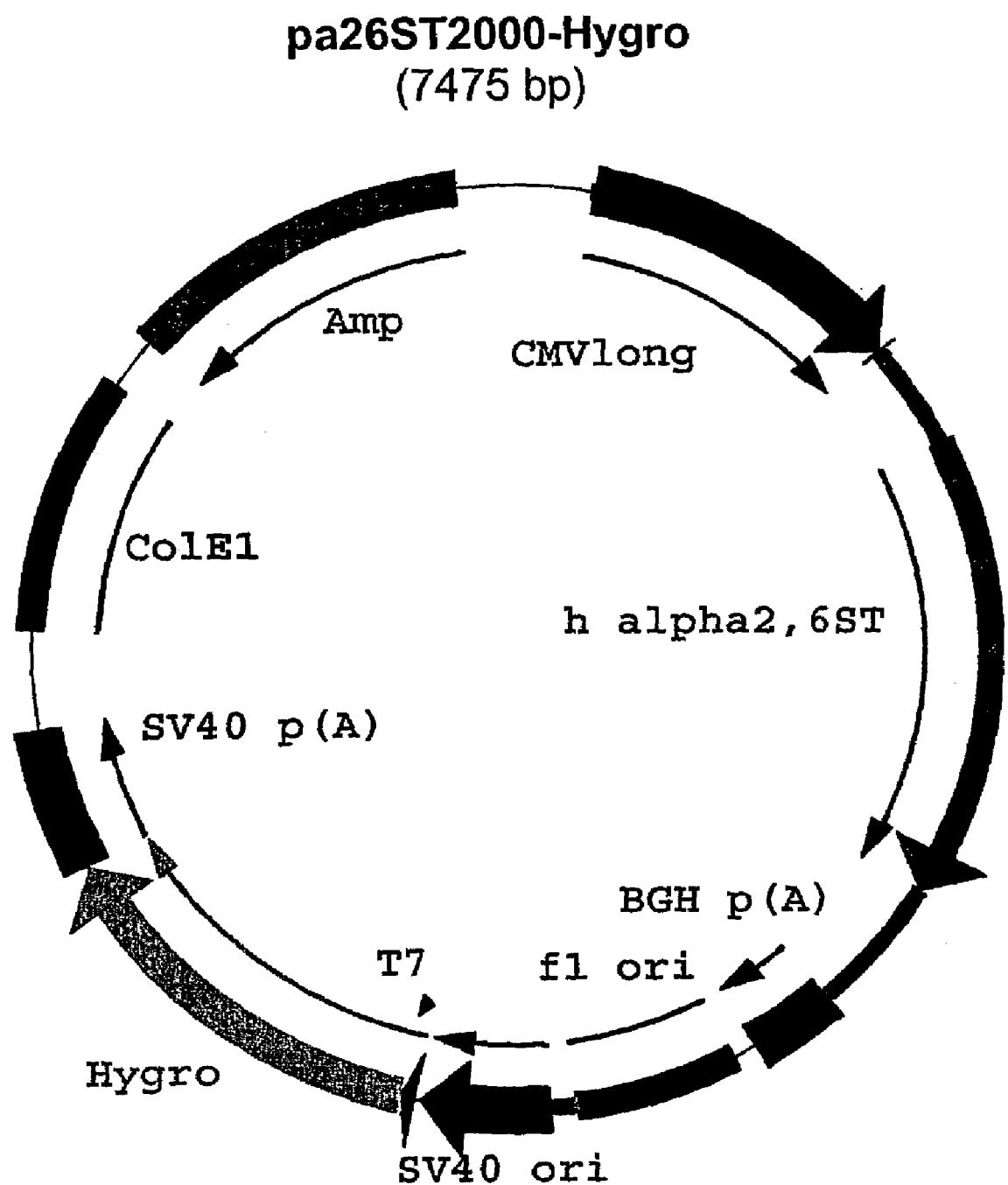
FIG. 1. Schematic representation of pAlpha2,6ST2000/Hygro.

Provided are methods for producing and/or propagating a virus particle, such methods comprising the steps of: contacting a cell with a virus particle in a culture medium under conditions conducive to infection of the cell by the virus particle; and culturing the aid cell under conditions conducive to propagation of the virus particle, wherein the cell over-expresses a nucleic acid encoding an alpha2,6 sialyltransferase or a functional equivalent thereof. The nucleic acid may encode an alpha2,6 sialyltransferase from different sources, such as rat and human. The alpha2,6 sialyltransferase may be human alpha2,6 sialyltransferase. Further provided are methods for producing and/or propagating a virus particle, such methods comprising the steps of: contacting a cell with a virus particle in a culture medium under conditions conducive to infection of the cell by the virus particle; and culturing the cell under conditions conducive to propagation of the virus particle, wherein the cell over-expresses a nucleic acid encoding an alpha2,3 sialyltransferase or a functional equivalent thereof. The nucleic acid may encode an alpha2,3 sialyltransferase from different sources, such as rat and human. The alpha2,3 sialyltransferase may be human alpha2,3 sialyltransferase. In certain embodiments, the virus particle is an influenza virus particle. Other non-limiting examples of virus particles that can be produced and/or propagated by using methods of the present invention are parainfluenza virus, Adeno-Associated virus (AAV) or polyomavirus. Any virus that utilizes the glycosylation structures that are induced by the alpha2,3 and alpha2,6 sialyltransferases can be propagated and/or produced by using methods of the present invention.

In a preferred embodiment, the invention provides methods for propagating an influenza virus particle, wherein said influenza virus particle is present in an influenza isolate. More preferred are methods, wherein said influenza isolate is obtained from at least one influenza-infected mammalian subject. Even more preferred, are methods for propagating an influenza virus particle, wherein said influenza-infected mammalian subject is human or pig. In another embodiment, the invention provides methods for producing and/or propagating an influenza virus particle, wherein said influenza isolate is obtained from at least one influenza-infected bird. Isolates as used herein refers to batches of influenza viruses that are obtained from subjects that are infected with influenza viruses. These subjects may be all species that are susceptible for influenza viruses, such as humans, birds, pigs and horses. Humans can get infected with influenza in different ways: either directly from other humans or directly from animal subjects such as pigs and birds. Propagated viruses that are used for vaccine manufacturing might be originally derived from one or more subjects (one or more human individuals, or one or more birds, pigs, etc.). In the case wherein influenza virus transmission from a bird to a human causes direct disease in humans, as was the case in the Hong Kong in 1997 (see above) it might be useful to be able to produce and/or propagate the influenza virus particles present in the bird isolate directly for vaccine manufacturing. The present invention provides methods for producing and/or propagating influenza virus particles present in isolates that are obtained from species such as birds, pigs, horses and humans by over-expressing the sialyltransferase proteins that are involved in the glycosylation of cell surface proteins and that generate the so-called SAalpha2,3Gal and SAalpha2,6Gal linkages in the oligosaccharide chains. Isolates as used herein preferably refers to clinical isolates (i.e., isolates obtained from diseased patients). Such clinical isolates are also referred to as primary isolates. Primary isolates can be influenza isolates directly obtained from, for instance, the nose, mucus and/or faeces of humans or animals that are infected with influenza virus(es). However, isolates that have been propagated on eggs on or cells or on other systems can still be further produced and/or propagated by methods of the present invention. Therefore, virus particles that are produced and/or propagated using the present invention may be present in passaged batches, but are preferably present in primary batches, such as clinical isolates.

In a preferred embodiment of the invention, the production and/or propagation of influenza virus particles is carried out by using cells in a culture medium, wherein said cell is transformed with E1 from adenovirus. More preferably, said cell is a human cell. In a highly preferred aspect, the invention provides methods for propagating an influenza virus particle according to the invention, wherein said human cell is PER.C6 or a derivative thereof.

PER.C6 cells are found to be useful for the propagation of different kinds of viruses such as rotavirus and influenza virus (see WO 01/38362). PER.C6 cells were first generated by transforming cells obtained from an embryonal retina with the E1 region of Adenovirus serotype 5. It was found that both alpha2,3 and alpha2,6 sialyltransferase proteins are present and active in PER.C6 cells (Pau et al. 2001). Therefore, virus particles that specifically interact with the sialic acid—galactose linkage of the 2,3 type as well as of the 2,6 type (SAalpha2,3Gal and SAalpha2,6Gal, respectively) were able to grow on PER.C6 cells. It is an important aspect of the invention that over-expression of either one of these sialyltransferase proteins leads to a specific propagation of sets of influenza viruses that either prefer the SAalpha2,3Gal residue or the SAalpha2,6Gal residue. This enables one to generate virus batches for vaccine production that have the best content for optimal protection. This content may differ. As discussed above, some spreading of the virus occurs mainly through human-human contact, while in others (such as the 1997 Hong Kong case, a direct bird-human contact was enough to sort a dramatic effect in humans. Depending on the virulence and the types of influenza viruses that play a role in this, a choice can be made for which set of virus particles in an isolate should be propagated with which the final vaccine is produced.

The present invention also provides methods for producing and/or propagating an influenza virus particle, wherein said nucleic acid encoding the sialyltransferase is heterologous to said cell. Preferably, said nucleic acid encoding the sialyltransferase is integrated into the genome of said cell. Heterologous as used herein means that the nucleic acid is manipulated such that the gene encoding the sialyltransferase expresses more of the protein than without said manipulation. Heterologous also means that the nucleic acid may be from a species that is different from the species from which the cell was derived, but may also be from the same species. A cell is said to over-express the sialyltransferase when the cell expresses more sialyltransferase than typical for that cell. A cell that over-expresses the sialyltransferase may also over-express the protein by manipulation of the genome of said cell such that the gene present in the genome of said cell expresses more of the protein than said cell did before it was manipulated. The over-expression may be induced by external means such as integration of a different or more-active promoter, by removal or inhibition of suppressors that normally limit the expression of the protein, or by chemical means. The over-expression may also be selected for. If cells are selected for a significant over-expression of at least one sialyltransferase they may be used for methods according to the present invention. Therefore, such cells and the use of such cells is also part of the present invention.

In another embodiment, the present invention provides methods for making a vaccine, said method comprising the steps of: producing and/or propagating a virus particle according to methods of the invention; and inactivating the virus particles so produced. Preferably said methods for making a vaccine further comprise the steps of: treating said virus particles so produced to yield antigenic parts; and obtaining at least one of said antigenic parts, preferably through means of purification and/or enrichment for said at least one part. Preferably a purified and/or enriched composition comprising said at least one obtained antigenic part does not comprise other antigenic parts of said treated virus particles. In a more preferred embodiment, the invention provides methods for making a vaccine, wherein said antigenic part comprises the hemagglutinin protein or a part thereof, and/or the neuraminidase protein or a part thereof from influenza virus. The neuraminidase (NA) and the hemagglutinin (HA) proteins are the most prominent antigenic parts of the influenza virus particle and are prone to differences during different propagation steps. The invention also provides vaccines obtainable according to methods of the present invention, while it also provides pharmaceutical compositions comprising a vaccine obtainable according to the present invention.

As mentioned, the cells of the present invention are extremely useful for the propagation of primary, clinical isolates comprising influenza virus particles, while said cells can also be applied for propagating isolates that already have been passaged on embryonated eggs or on other systems, to obtain a selection of influenza virus particles that recognize specific glycosylation residues present on glycoproteins. Thus, the present invention also provides the use of a cell line over-expressing an alpha2,6 sialyltransferase or a functional part thereof for the propagation of a virus particle and the use of a cell line over-expressing an alpha2,3 sialyltransferase or a functional part thereof for the propagation of a virus particle. Preferably, said virus particle is an influenza virus particle. More preferably, said influenza virus particle is present in an influenza isolate obtained from at least one influenza-infected mammalian subject. Even more preferred, are uses of said cell line according to the present invention, wherein said influenza-infected mammalian subject is a human or a pig, whereas it is also preferred that said influenza virus particle is present in an influenza isolate obtained from at least one influenza-infected bird.

The present invention further provides a method for selective production and/or propagation of a set of predetermined virus particles present in an isolate, wherein said set of predetermined virus particles has a preference for a specific glycosylation moiety present on a receptor, and wherein said isolate comprises in addition to said set also virus particles not having said preference, said method comprising the steps of: incubating a cell which is capable of expressing and exposing said receptor comprising said specific glycosylation moiety, with said isolate in a culture medium under conditions conducive to infection of said cell by at least one virus particle present in said set; culturing said cell under conditions conducive to propagation of said virus particle; and harvesting virus particles so produced from said cell and/or said culture medium. A glycosylation moiety as used herein refers to any kind of residue, linkage and/or group of sugar types present in a oligosaccharide chain on a glycoprotein that is recognized by a virus particle for infection. Preferably, said glycosylation moiety comprises a SAalpha2,6Gal residue or a SAalpha2,3Gal residue. More preferred are methods wherein said set of predetermined virus particles is a set of predetermined influenza virus particles. The SAalpha2,6Gal residue and SAalpha2,3Gal residues are specifically recognized by the HA protein of the virus particle, in the case of influenza. It depends on the HA protein whether there is any specificity in the interaction with either one residue. In general, influenza isolates comprise viruses that interact specifically with the SAalpha2,6Gal residue as well as viruses that specifically interact with the SAalpha2,3Gal residue. With the present invention it is now possible to selectively propagate either set of viruses from clinical, primary and/or passaged isolates to obtain propagated sets of viruses that are useful in the production of an influenza vaccine, useful in humans. Besides the fact that vaccines can be produced for humans, it is also possible by using methods and means of the present invention to selectively propagate viruses for the manufacturing of veterinary applications to, for instance, prevent the spreading of influenza viruses through swine or horse populations. Preferably, said influenza isolate is obtained from at least one influenza-infected human, pig or bird. It is also preferred that said cell is a human cell and that it is transformed with E1 from adenovirus. Highly preferred are cells that are PER.C6 cells or derivatives thereof. Derivatives, as used herein, refer to modified versions of the original PER.C6 cells, wherein for instance other heterologous nucleic acids are introduced, knocked out, or in other ways modified. Non-limiting examples of PER.C6 derivatives are PER.C6 cells that stable express a temperature-sensitive mutant of Adenovirus E2A, or that express other adenovirus nucleic acids such as E4. If certain nucleic acids in PER.C6 cells have been switched on or off by other means such as chemical treatment or knockout techniques, these cells still remain PER.C6 derivatives. Although the examples provided describe the use of cells that over-express the erythropoietin (EPO) protein, it should be noted that it is not a part of the invention to have over-expression of EPO in the cells of the invention.

In another preferred embodiment, the invention provides methods for selective propagation of a set of virus particles present in an isolate, wherein said cell comprises a nucleic acid encoding a sialyltransferase that is heterologous to said cell. Even more preferred are methods according to the present invention, wherein said nucleic acid encoding a sialyltransferase is integrated into the genome of said cell. Such an integrated nucleic acid is preferably stably integrated through the use of selection markers such as the hygromycin and neomycin resistance genes.

The present invention also provides human cells comprising a heterologous nucleic acid encoding an alpha2,6 sialyltransferase or an alpha2,3 sialyltransferase. Preferably, said nucleic acid is integrated into the genome of said human cell. The invention also provides the use of such cells for the selective propagation of virus particles, preferably being influenza virus particles.

The present invention provides optimization of a process for propagation of primary isolates of human influenza virus. Also, the present invention provides optimization of a process for propagating primary as well as laboratory isolates of influenza viruses using the SAalpha2,6Gal or SAalpha2,3Gal (or both) glycosylation moieties present on cell surface glycoproteins. In general, human influenza viruses recognize the SAalpha2,6Gal moiety, while the avian influenza viruses recognize the SAalpha2,3Gal moiety. The swine influenza viruses generally utilize both residues. The invention provides optimization of a process for propagation of any virus for which the replication depends on the activity of alpha2,3 sialyltransferase and/or alpha2,6 sialyltransferase, or more generally, on the presence of SAalpha2,3Gal or SAalpha2,6Gal residues. The methods of the present invention comprise the use of cells in a culture medium. As an example of such a process, human cells were taken that are known to support efficient replication and production of influenza viruses.

The cells of the present invention are not only useful for the propagation of influenza viruses. It is well known in the art that other viruses such as Adeno-Associated Virus (AAV), human polyomavirus and parainfluenza viruses utilize the alpha2,3 and alpha2,6 linkages in glycoproteins for infection (Liu et al. 1998; Suzuki et al. 2001; Walters et al. 2001). Therefore, also provided are methods for production, selective production, and/or propagation of other viruses that use these glycosylation structures for recognition and infection of the targeted cell. Furthermore, also provided is the use of the cells of the invention and the methods and means for the production of viruses other than influenza and for the production of vaccines against such viruses, if applicable. The invention, therefore, also provides vaccines against viruses that utilize the SAalpha2,3Gal and the SAalpha2,6Gal residues for cellular recognition and infectivity.

It has been previously demonstrated that PER.C6™ cells (ECACC deposit 96022940) represent an ideal substrate for the propagation of influenza virus and that the production levels from PER.C6 resulted in high-titer preparations suitable for vaccine purposes (WO 01/38362). A novel cell line provided by the present invention, named "PER.C6-alpha2,6ST" is derived from PER.C6 through the following process: a plasmid harboring a nucleic acid encoding human alpha2,6 sialyltransferase under the control of the strong CMV promoter was transfected into PER.C6 cells and cells were subsequently selected for stable integration of the plasmid. The PER.C6-alpha2,6ST cells are characterized by the higher expression of SAalpha2,6Gal-containing receptors as compared to the number of receptors carrying the SAalpha2,6Gal residue in the original PER.C6 cells. This does not directly imply that the proteins carrying such moieties are over-expressed, but that the percentage of proteins carrying the SAalpha2,6Gal residue is higher than the percentage of such proteins in PER.C6 cells. PER.C6 cells are without over-expression of the alpha2,6 sialyltransferase already capable of expressing both SAalpha2,3Gal and SAalpha2,6Gal residues on cell surface glycoproteins. It is, however, an important aspect of the present invention to increase the percentage of proteins carrying the SAalpha2,6Gal residue in comparison to the percentage of proteins that carry the SAalpha2,3Gal residue. Due to direct substrate competition in the intracellular glycosylation machinery, receptors of the SAalpha2,3Gal type become under represented on the cell surface of cells over-expressing the alpha2,6 sialyltransferase protein. These combined characteristics make this new cell line an ideal medium for propagating primary influenza virus isolates without inducing selection pressure in the wild-type population. The propagation of such isolates on the cells of the present invention results in efficient production of large virus stocks with unaltered HA specificity and immunogenicity that are highly useful for the production of vaccines. As virus produced in PER.C6-alpha2,6ST does not present mutations resulting from adaptation to the SAalpha2,3Gal receptor (as is the case for embryonated eggs), the immunogenic properties of this virus are most comparable with those of naturally circulating influenza viruses. Consequently, vaccine preparations obtained from influenza virus grown on PER.C6-alpha2,6ST are ideally suited to induce a protective response against circulating wild-type influenza virus. It is known in the art that human influenza viruses are of the type recognizing the SAalpha2,6Gal linkages and it is, therefore, recognized in the art that it is desired to obtain vaccines comprising proteins from these viruses in order to sort a more protective immune response in humans (Newman et al. 1993).

If human influenza viruses are propagated via embryonated chicken eggs, virus variants that are able to bind specifically to SAalpha2,3Gal will be selected for, and the SAalpha2,6Gal recognizing viruses will be selected out. PER.C6 cells have both SAalpha2,6Gal and SAalpha2,3Gal containing receptors at its surface. For a preferred propagation of the SAalpha2,6Gal recognizing viruses it is, therefore, preferred to have over-expression of receptors that harbor this component, as discussed above. To determine the effect of the opposite, namely over-expression of human alpha2,3 sialyltransferase, the present invention also provides methods and means for generating another novel cell line named "PER.C6-alpha2,3ST." These cells are derived from PER.C6 in a similar manner as described above for the PER.C6-alpha2,6ST cells, by transfection of a plasmid harboring nucleic acid encoding human alpha2,3 sialyltransferase under the control of the strong CMV promoter, after which, cells carrying a stable integration of the plasmid are selected. A PER.C6-alpha2,3ST cell is characterized by the higher expression of SAalpha2,3Gal-containing receptors.

Both alpha2,6 sialyltransferase and alpha2,3 sialyltransferase over-expressing cell lines are useful since alpha2,6 sialyltransferase over-expressing cells can be used for the propagation of influenza viruses that preferably recognize the SAalpha2,6Gal residue, while the alpha2,3 sialyltransferase over-expressing cells can be used for the propagation of influenza viruses that preferably recognize the SAalpha2,3Gal residue. When the infection and the spreading of the viruses mainly occurs via human-human contact and the viruses become more adapted to the infectious route via the SAalpha2,6Gal residues, then it is preferred to apply the alpha2,6 sialyltransferase over-expressing cell line. On the other hand, when the infectivity occurs directly from birds that do not have glycoproteins harboring the SAalpha2,3Gal residue to humans (as was the case in the small but severe epidemic in Hong Kong in 1997) then it is preferred to apply cells that over-express the alpha2,3 sialyltransferase.

As used herein, the terms alpha2,6 sialyltransferase or alpha2,3 sialyltransferase refer to the respective transferases and also to equivalents of said transferase, wherein said equivalents comprise the same transferase activity in kind, not necessarily in amount, as the transferase it is equivalent to. Suitable equivalents can be generated by the person skilled in the art. A part of said transferase is a suitable equivalent if it comprises the same transferase activity in kind not necessarily in amount. Other suitable equivalents are derivatives and/or analogues of alpha2,3 sialyltransferase or alpha2,3 sialyltransferase comprising the same transferase activity in kind, not necessarily in amount, as the transferase it is equivalent to. Such derivatives may be generated through conservative amino acid substitution or otherwise. A derivative can also be made from a part of the respective transferases.

An influenza virus particle, as used herein, can be an influenza virus or an influenza virus-like particle. An equivalent of an influenza virus particle is a virus (like) particle comprising the same infectivity properties in kind, not necessarily in amount, as an influenza virus particle. Such equivalents can, for instance, be generated by recombinant means. Such equivalents may comprise molecules not typically present in an influenza virus.

EXAMPLES

Example 1

Construction of pAlpha2,6ST2000/Hygro

The fragment containing the sequence coding for alpha2,6 sialyltransferase was obtained by EcoRI digestion of plasmid pGST-Gal (a gift from Dr. I. van Die, Free University of Amsterdam. The plasmid consists of a pBR322 backbone containing the entire cDNA sequence coding for rat alpha2,6 sialyltransferase, GenBank accession nr. M18769). The fragment was made blunt-ended by T4 DNA polymerase according to standard procedures. After gel purification, the alpha2,6 sialyltransferase encoding fragment was ligated into pcDNA2000/Hygro (also known as plasmid pcDNA2000/Hyg(-) which has been described in WO 00/63403), which was linearized with PmeI, dephosphorylated and gel purified according to standard laboratory procedures. The resulting plasmid was named pAlpha2,6ST2000/Hygro (FIG. 1).

Example 2

Transfection of pAlpha2,6ST2000/Hygro in PER.C6-EPO and Selection of Over-expressing Clones PER.C6-EPO were initially generated for other purposes, namely for experiments focusing on glycosylation of erythropoietin (EPO). EPO is a protein involved in stimulation of erythropoiesis and its activity depends heavily on its sialic acid content for in vivo functionality. The PER.C6-EPO cell line is a derivative of PER.C6 and overexpresses the human EPO protein (cells have been described in WO 00/63403). The fact that this cell line is producing EPO is not believed to be critical for the present invention. PER.C6-EPO cells were cultured and transfected with pAlpha2,6ST2000/Hygro, as described below.

Figure 4:
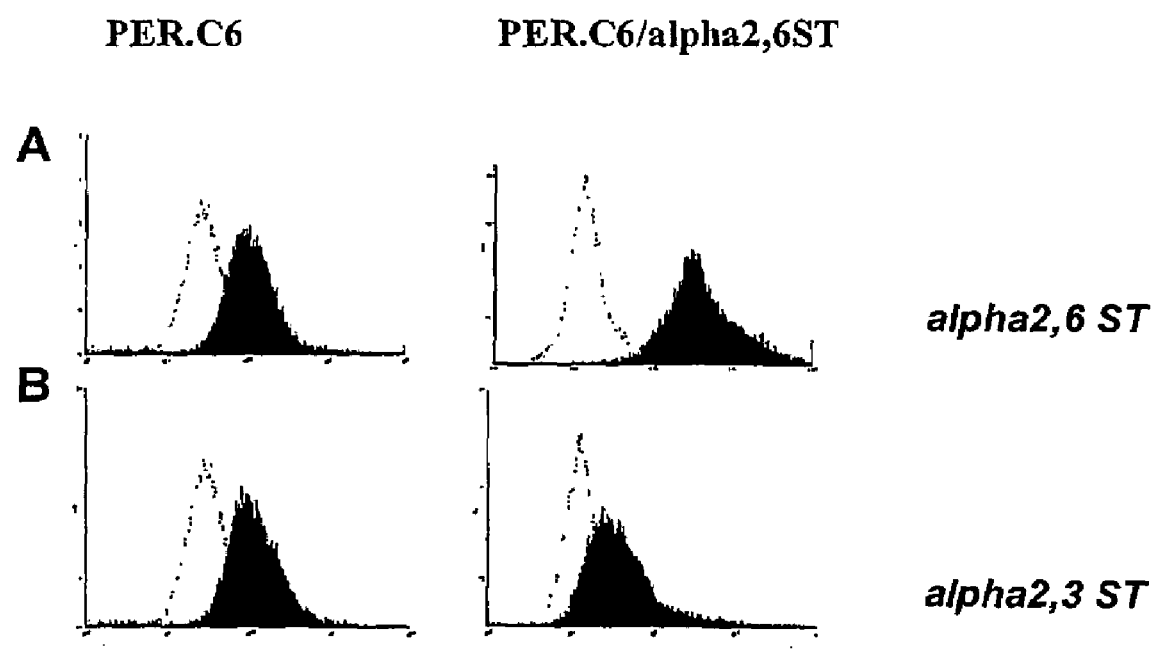
FIG. 4. Detection of (A) SAalpha2,6Gal and (B) SAalpha2,3Gal in PER.C6 and PER.C6/alpha2,6ST by FACS analysis.

PER.C6 cells were seeded in tissue culture dishes (10 cm diameter) with approximately 2-3 million cells/dish and were kept overnight at 37° C. and 10% $CO_2$. On the next day, cells are transfected using Lipofectamine (Gibco) according to the manufacturer's protocol. Twenty dishes were transfected each with 2 µg of pAlpha2,6ST2000/Hygro all, according to standard protocols, well known to persons skilled in the art. Another 6 dishes served as negative controls for hygromycin killing and transfection efficiency. On the next day, hygromycin was added to the dishes at a concentration of 50 µg/ml, dissolved in DMEM medium containing FES. Cells were incubated over a period of 3-4 weeks, with regular washing of the cells with fresh medium supplemented with hygromycin. Cells were monitored daily for death, comparing with the negative controls that did not receive the plasmids harboring the hygromycin selection markers. Outgrowing colonies were picked and subcultured generally as described for erythropoietin- and antibody-overexpressing cell lines in WO 00/63403. Approximately 25 selected antibiotic-resistant colonies were grown subsequently in 24-wells, 6-wells plates and T25 flask without hygromycin. When cells reached growth in T75 tissue culture flasks at least one vial of each clone was frozen and stored for backup. The clones were subsequently tested for alpha2,6ST activity by FACS analysis on a FACsort apparatus (Becton Dickinson) using methods previously described by Govorkova et al. (1999). For this, the SAalpha2,6Gal-specific *Sambucus nigra* agglutinin (DIG Glycan differentiation kit, Roche) was used following the supplier's protocols. These clones were subcultured in a time span of two months, during which FACS analysis experiments were performed on a regular basis to monitor expression of alpha2,6 sialyltransferase on the cell surface. Increased expression of SAalpha2,6Gal was stable. The best alpha2,6 sialyltransferase-expressing clone, as assessed by the highest density of SAalpha2,6Gal on the cell surface, was clone 25-3.10. This clone was named "PER.C6-alpha2,6 ST." The results in FIG. 4A show a FACS analysis on PER.C6-alpha2,6 ST at the end of the selection process. It is evident that stable transfection of pAlpha2,6ST2000/Hygro leads to markedly increased levels of SAalpha2,6Gal residues on the cell surface as compared to the maternal PER.C6 cell line. Interestingly, over-expression of alpha2,6 sialyltransferase also seems to result in lower amounts of SAalpha2,3Gal residues, as detected by FACS using alpha2,3Gal-specific *Maackia amurensis* agglutinin (FIG. 4B). This effect is most likely due to competition of alpha2,6 sialyltransferase with endogenous alpha2,3 sialyltransferase for the same glycoprotein substrate.

Example 3

Generation of alpha2,6- and alpha2,3 Sialyltransferase cDNA Expression Vectors

Figure 2A:
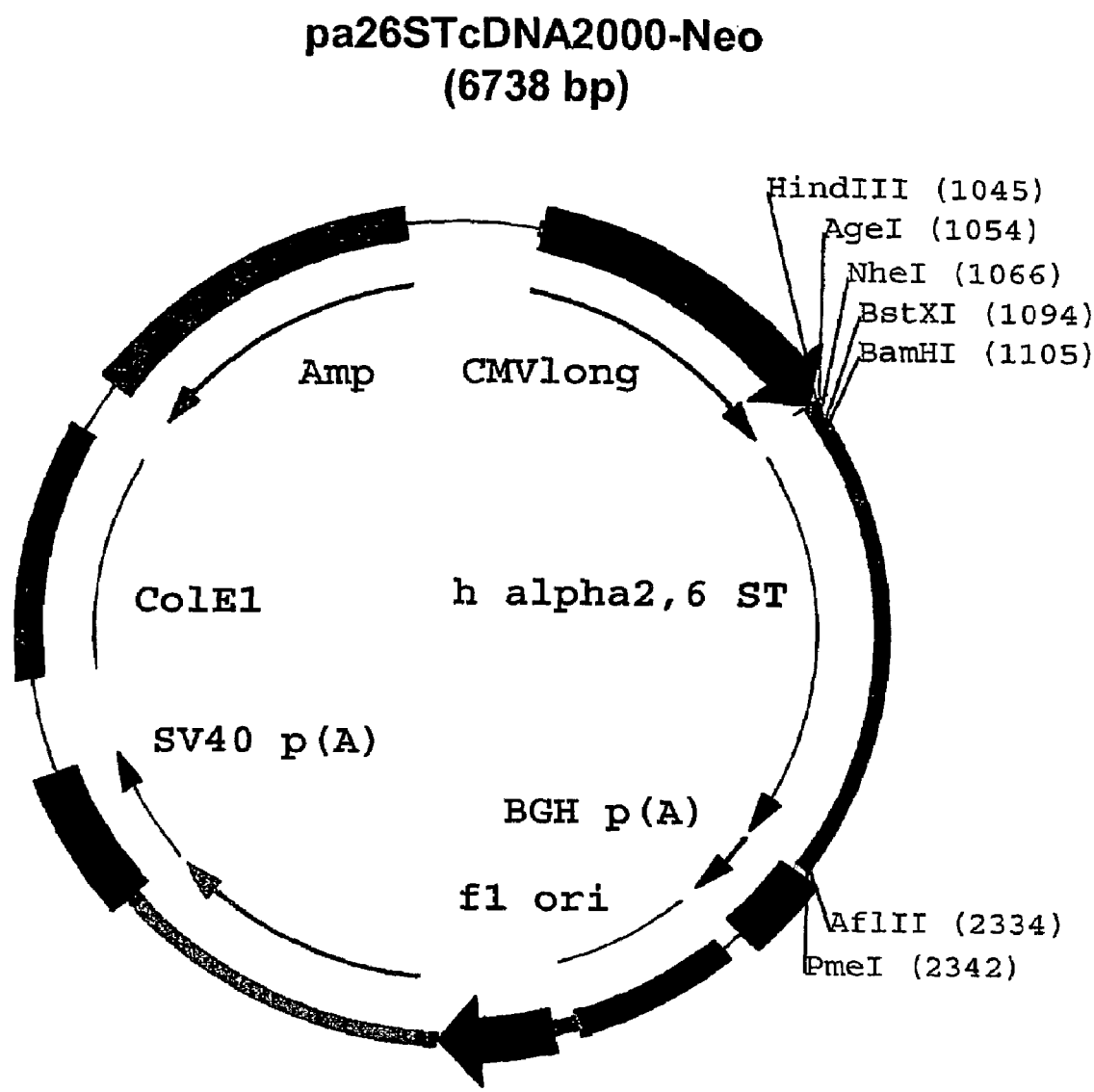
FIG. 2. Schematic representation of (A) pAlpha2,6STcDNA2000/Neo and (B) pAlpha 2,6STcDNA2000/Hygro.
Figure 2B:
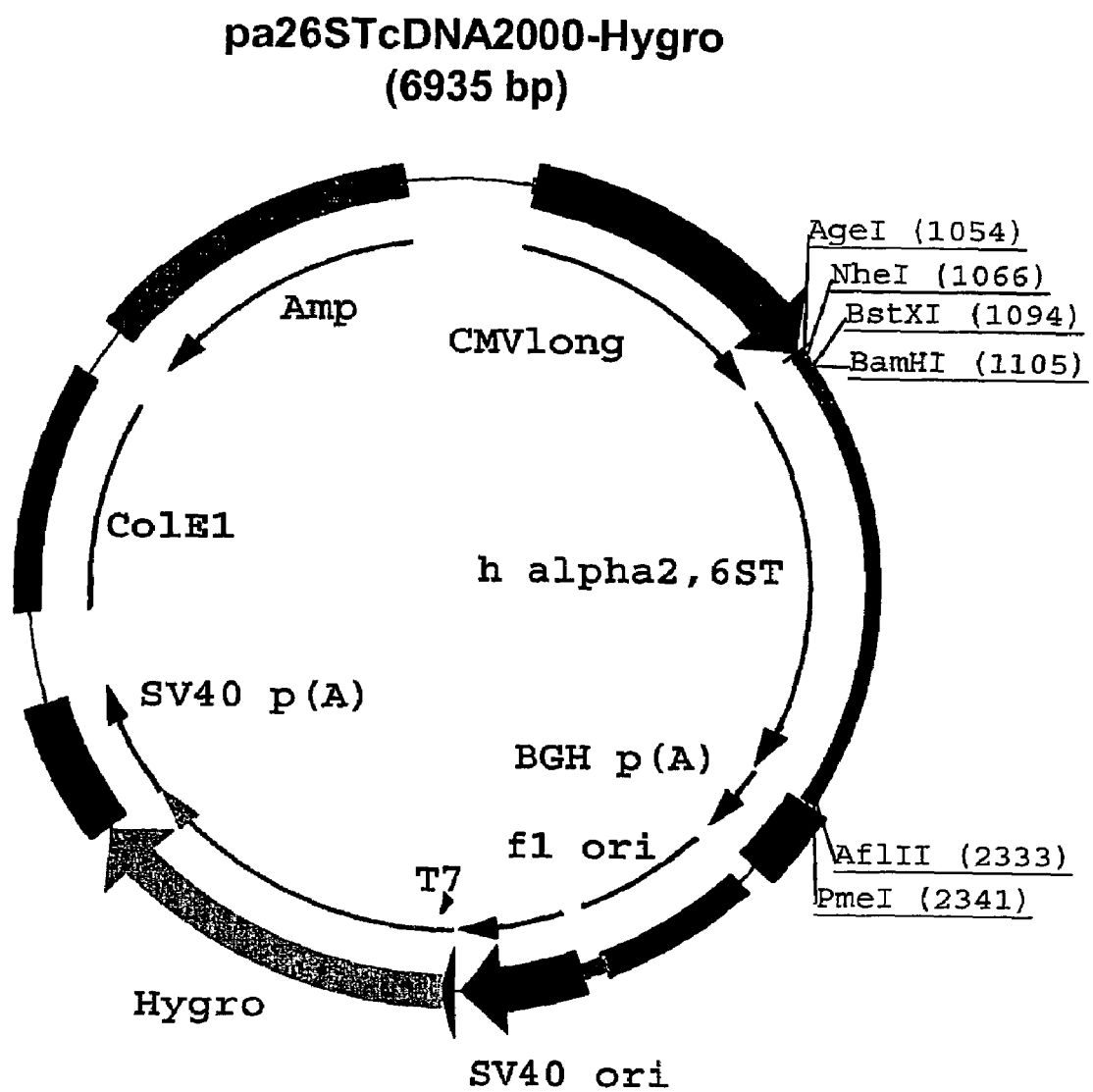

A PCR fragment containing the full length cDNA of human alpha2,6 sialyltransferase (GenBank accession nr. 14735135) is obtained by Polymerase Chain Reaction (PCR) on a human cDNA library using methods well known to persons skilled in the art. The primers used for the amplification (sense: 5'-TTT TTT GGA TCC ATG ATT CAC ACC AAC CTG AAG AAA AAG-3' SEQ ID NO: 1, antisense: 5'-TTT TTT CTT AAG TTA GCA GTG AAT GGT CCG GAA GC-3' SEQ ID NO: 2) contain an additional 5'-tail that allows digestion with BamHI in the sense primer and AflII in the antisense primer, respectively. The PCR product is purified via agarose gel electrophoresis and digested with BamHI and AflII and, subsequently, cloned into pcDNA2000/Hygro (described as pcDNA2000/Hyg(−) in WO 00/63403) and into pcDNA2000/Neo (this vector was basically constructed in the same way as pcDNA2000/Hyg(−) from pcDNA2000/DHFR as has been described in detail in WO 00/63403). For this, pcDNA2000/Hygro and pcDNA2000/Neo were also digested with BamHI and AflII restriction enzymes. The sequence and the correct cloning are checked by double-stranded sequencing according to standard procedures known to persons skilled in the art of molecular biology. The resulting plasmids are named pAlpha2,6STcDNA2000/Hygro (FIG. 2A) pAlpha2,6STcDNA2000/Neo (FIG. 2B). They comprise nucleic acid encoding human alpha2,6 sialyltransferase under the control of the extended CMV promoter (see WO 00/63403). Furthermore, the plasmids confer resistance to neomycin and hygromycin, respectively, that are used to select for clones that have integrated the plasmid into their genome in a stable manner.

Figure 3A:
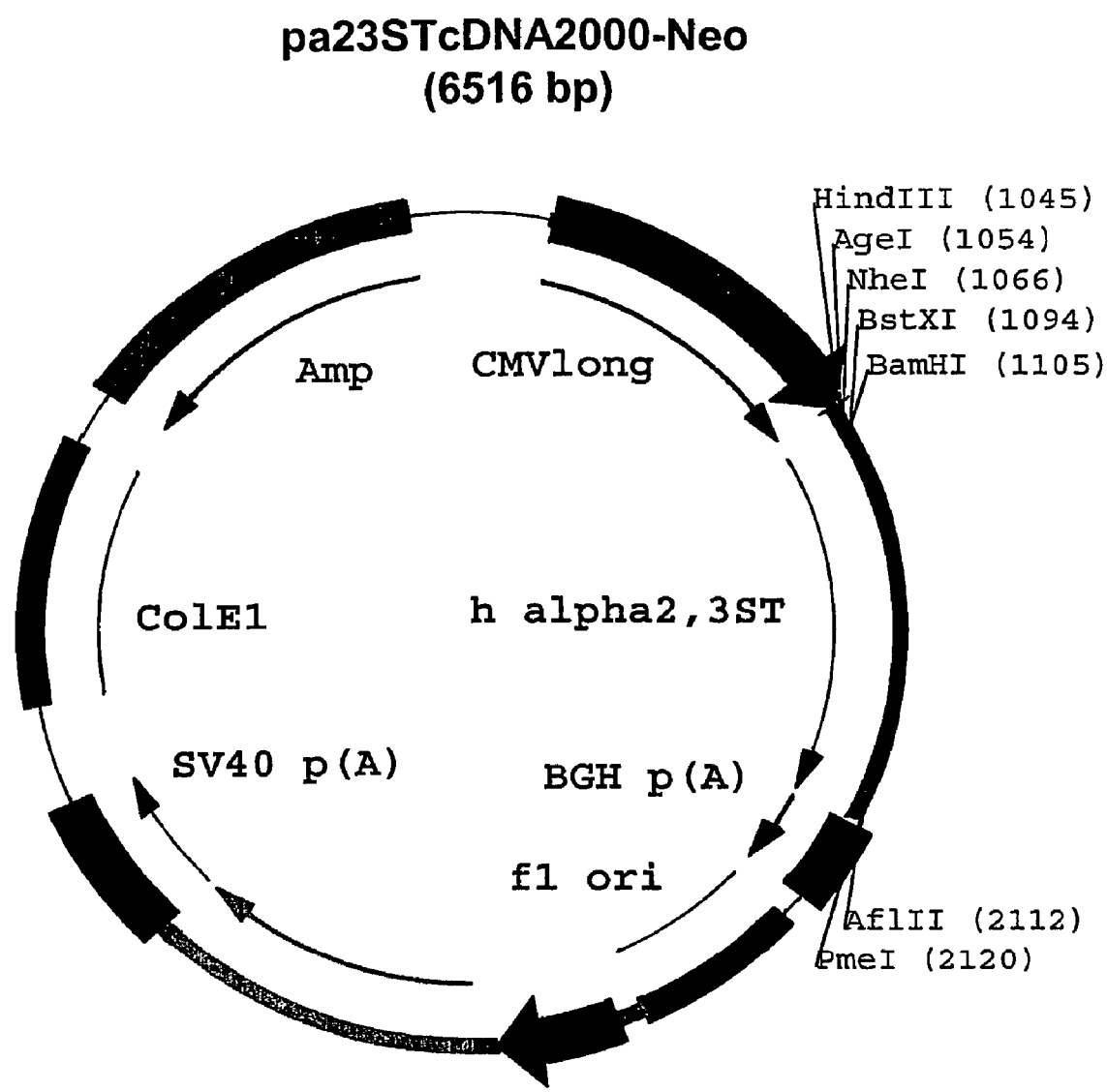
FIG. 3. Schematic representation of (A) pAlpha2,3STcDNA2000/Neo and (B) pAlpha2,3STcDNA2000/Hygro.
Figure 3B:
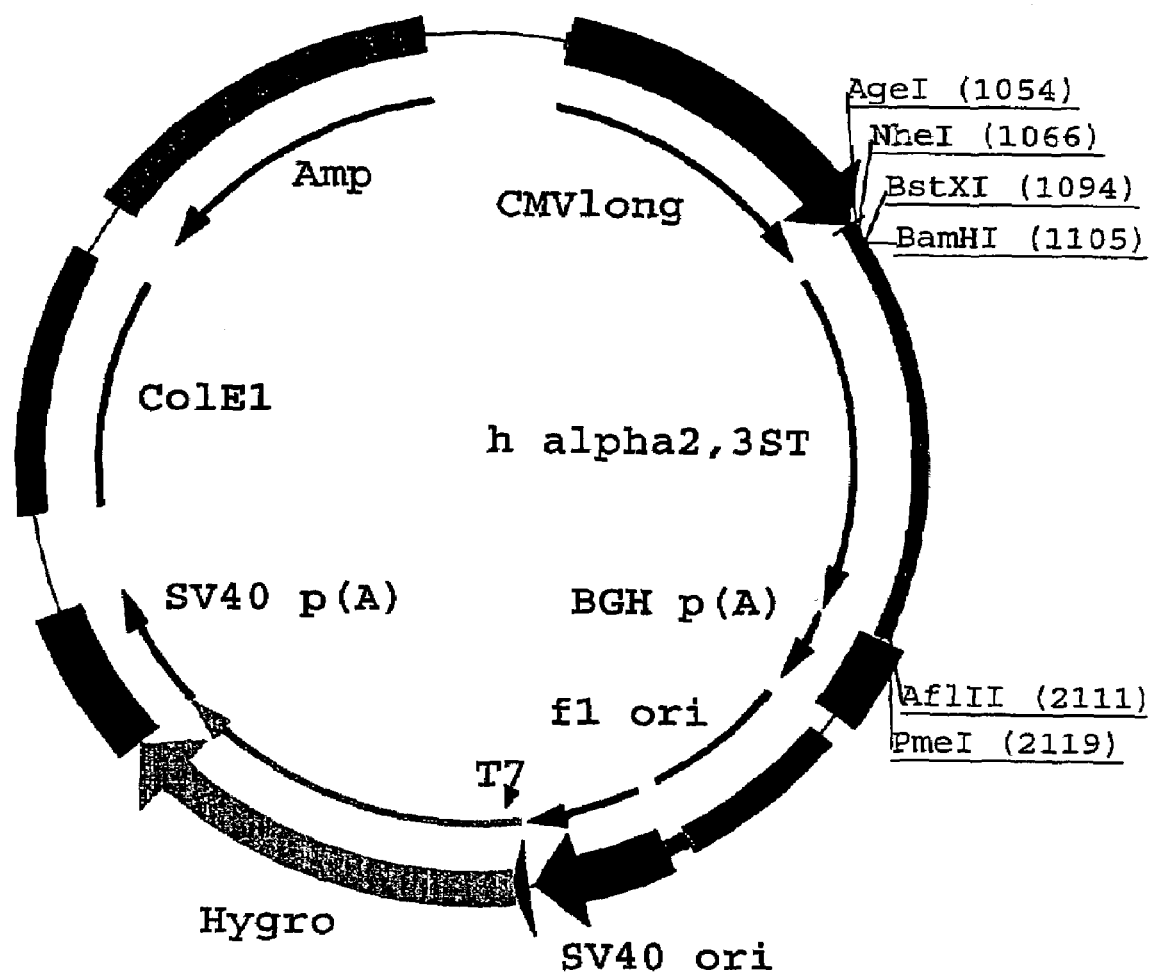

The cDNA of human alpha2,3 sialyltransferase (GenBank accession nr. L23767) is obtained and cloned as described above for the human alpha2,6 sialyltransferase gene. The primers that are used for the PCR reaction are: sense 5'-TTT TTT GGA TCC ATG TGT CCT GCA GGC TGG AAG CTC-3', SEQ ID NO: 3, and antisense 5'-TTT TTT CTT AAG TCA GAA GGA CGT GAG GTT CTT GAT AG-3', SEQ ID NO: 4. The resulting plasmids are named pAlpha2,3STcDNA2000/Hygro (FIG. 3A) pAlpha2,3STcDNA2000/Neo (FIG. 3B).

Example 4

Generation of Stable PER.C6 Cells Over-expressing Either Human alpha2,6- or Human alpha2,3 Sialyltransferase Cells of the PER.C6 cell line are seeded in 40 tissue culture dishes (10 cm diameter) with approximately 2-3 million cells/dish and are kept overnight at 37° C. and 10% $CO_2$. On the next day, cells are transfected using Lipofectamine (Gibco) according to the manufacturer's protocol and to standard culturing procedures known to persons skilled in the art. Twenty dishes are transfected each with 5 µg of pAlpha2,6STcDNA2000/Neo. Another 20 dishes with non-transfected cells serve as negative controls for neomycin killing and transfection efficiency. On the next day, neomycin (0.5 mg/ml) is added to the appropriate dishes, dissolved in medium containing FBS. Cells are incubated over a period of 4-5 weeks, with regular washing of the cells with fresh medium supplemented with the selection agent. Cells are monitored daily for death, comparing with the negative controls that did not receive the plasmids harboring the neomycin and hygromycin selection markers. Outgrowing colonies are picked and subcultured generally as described for erythropoietin- and antibody-overexpressing cell lines in WO 00/63403.

From each cell line, approximately 50 selected neomycin-resistant colonies are grown subsequently in 96-wells, 24-wells, 6-wells plates and T25 flask with neomycin. When cells reach growth in T25 tissue culture flasks at least one vial of each clone is frozen and stored for backup. Each clone is subsequently tested for production of recombinant human alpha2,6 sialyltransferase by FACS analysis using SAalpha2,6Gal-specific *Sambucus nigra* agglutinin as described above and as previously described by Govorkova et al. (1999). The following selection of good producer clones is based on expression, culturing behavior and viability. To allow checks for long-term viability, suspension growth in roller bottles and bioreactor during extended time periods, more vials of the best performing clones are frozen, and are selected for further investigation. These clones are subcultured in a time span of two months. During these two months, FACS analysis experiments are performed on a regular basis to monitor expression of alpha2,6 sialyltransferase on the cell surface. The best stable producer is selected and used for cell banking. This clone is expanded to generate a cell line that is named PER.C6-H-alpha2,6 ST.

Cell lines over-expressing the human alpha2,3 sialyltransferase protein are generated in generally the same way as described above for the human alpha2,6 sialyltransferase over-expressing PER.C6 cells. In this case, plasmid pAlpha2,3STcDNA2000/Neo is used. The resulting cell line is named PER.C6-H-alpha2,3 ST.

Example 5

Cell Culture and Infection with Primary and Adapted Influenza Virus Isolates in PER.C6 Cells and in alpha2,6 Sialyltransferase-overexpressing PER.C6 Cells Experiments were performed to compare the susceptibility to infection of PER.C6 with that of PER.C6-alpha2,6 ST. Suspension cultures of PER.C6 and PER.C6-alpha2,6 ST were cultured in serum-free ExCell 525 medium (JRH Biosciences) supplemented with 4 mM L-Glutamin (Gibco), at 37° C. and 10% $CO_2$ in 490 $cm^2$ tissue culture roller bottles during continuous rotation at 1 rpm. The procedure described below was applied for all the influenza infections reported. At the day of infection, cells were seeded in 6-well plates, at the density of $1 \times 10^6$ cells/ml in a final volume of 2 ml of serum-free media, containing 2 mg/ml Pen/Strep (Gibco), 200 mg/ml Fungizone (Gibco) and 3 µg/ml trypsin-EDTA (Gibco). Cells were infected with a viral inoculum of a primary isolate and with a PER.C6-adapted batch (derived from the primary isolate and passaged for 1 passage on PER.C6 cells). The primary isolate that was used is the A/Netherlands/002/01 (H1N1, A/New Caledonia like, gift from Prof. Dr. A. Osterhaus, University of Rotterdam). Both batches were used at a $10^{-2}$ v/v dilution. Infected cells were kept in static culture at 35° C., in 10% $CO_2$, for six days. Viral supernatants were retrieved throughout the experiment and subsequently clarified. Clarification was performed by pelleting the cells in a microfuge at 5,000 rpm for 5 min, at room temperature. Cell pellets were analyzed by direct immunofluorescence assay as described infra. Supernatants were transferred to a new eppendorf tube, rapidly frozen in liquid $N_2$ and stored at −80° C. until use in plaque assays (see below).

Example 6

Immunofluorescence Test

Figure 5:
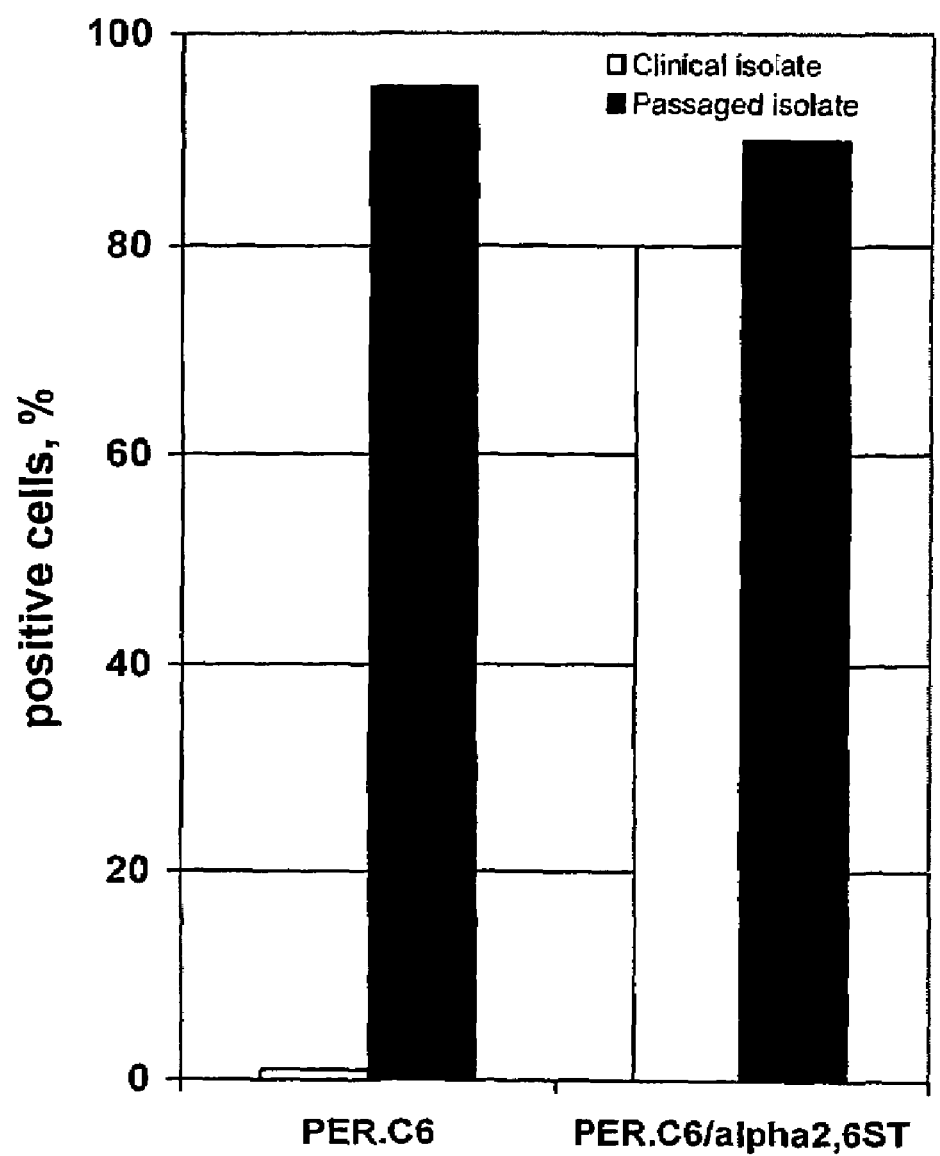
FIG. 5. Propagation of a primary clinical influenza isolate and a egg-passaged influenza batch (from the same primary isolate) on PER.C6 and PER.C6/alpha2,6ST, determined by fluorescence. Infectivity is expressed as percentage of cells positive for HA-immunofluorescent staining.

Direct immunofluorescence (I.F.) assays for the detection of Influenza virus infection were carried out in infected cells (see above) using the IMAGEN™ Influenza Virus A and B kit (Dako) according to the protocol provided by the supplier. Briefly, infected cells were centrifuged for 5 min. The supernatant was removed and the pellet resuspended in PBS. This was repeated twice to wash the cells thoroughly. The washed cell pellet was resuspended in PBS and 20 µl of cell suspension was added to each of two wells of an I.F. slide. This was allowed to dry at room temperature. The cells were fixed by adding 20 µl acetone to each well and air-dried. To each well, 20 µl of the appropriate IMAGEN Influenza reagent (i.e., labeled antibody specific Influenza A or B) was added. The slide was then incubated for 15 min at 37° C. on a damp tissue. Excess reagent was washed away with PBS and then rinsed for 5 min in PBS. The slide was air-dried at room temperature. One drop of IMAGEN mounting fluid was added to each well and a cover slip placed over the slide (this was fixed in place with a small amount of nail polish). Samples were viewed microscopically using epifluorescence illumination. Infected cells were characterized by a bright apple-green fluorescence. The approximate percentage of cells that show positive (fluorescent green) compared with negative (red) cells was recorded. Results are shown in FIG. 5. It is evident that PER.C6-alpha2,6 ST supported efficiently the replication of the clinical isolate (white bars).

Example 7

Plaque Assay

Figure 6:
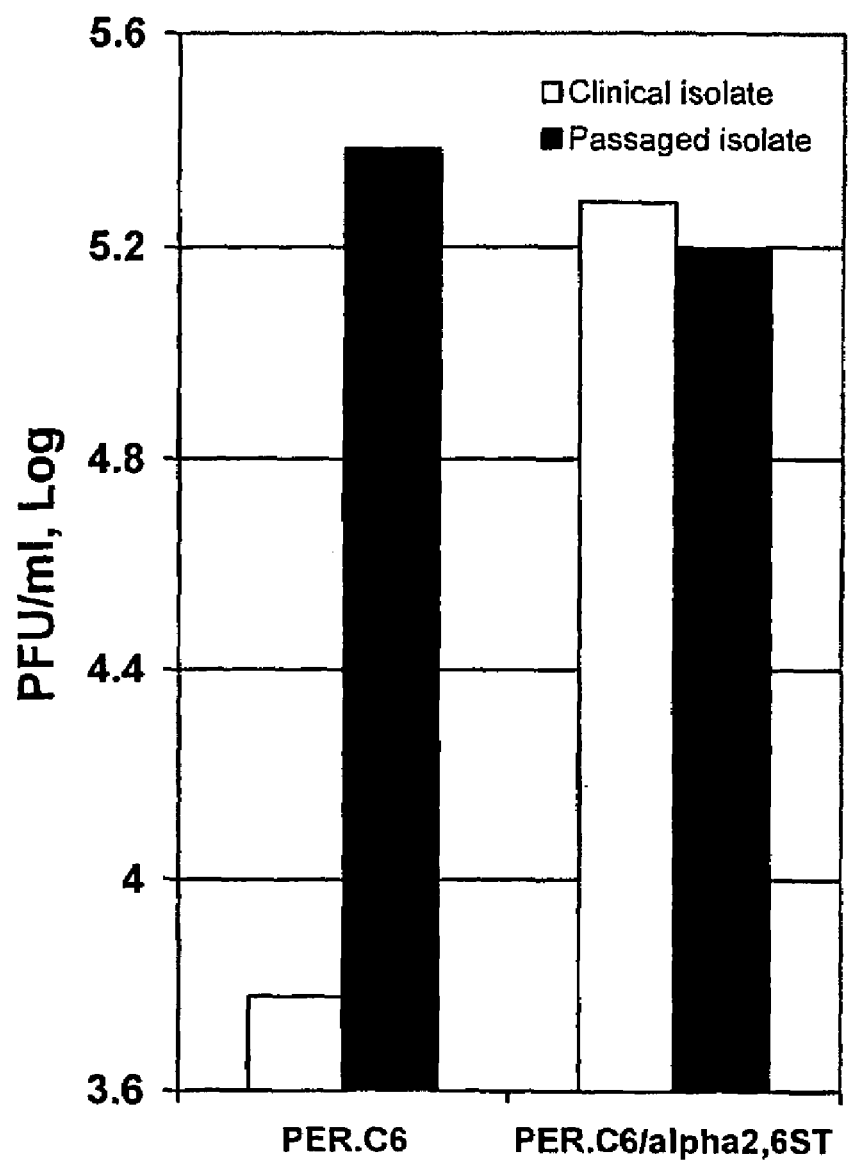
FIG. 6. Propagation of a primary clinical influenza isolate and a egg-passaged influenza batch (from the same primary isolate) on PER.C6 and PER.C6/alpha2,6ST, determined by plaque assay. Infectivity is expressed as plaque-forming units (pfu's) per ml.

Virus production in PER.C6 and PER.C6-alpha2,6 ST were studied by scoring for plaque formation in MDCK (Madin Darbin Canine Kidney) cells inoculated with virus supernatants. MDCK cells are particularly useful for such plaque assay experiments. A total of 1 ml of 10-fold diluted viral supernatants of primary and PER.C6-passaged influenza virus both propagated on PER.C6 and PER.C6-alpha2,6 ST according to the methods described in Example 5, were inoculated on MDCK cells which were grown until 95% confluence in 6-well plates in DMEM supplemented with 2 mM L-glutamin. After 1 h at 37° C. the cells were washed twice with PBS and overloaded with 3 ml of agarose mix (1.2 ml 2.5% agarose, 1.5 ml 2×MEM, 30 µl 200 mM L-Glutamine, 24 µl trypsin-EDTA, 250 µl PBS). The cells were then incubated in a humid, 10% $CO_2$ atmosphere at 37° C. for approximately 3 days and viral plaques were visually scored and counted. Results are shown in FIG. 6. The clinical isolate of influenza virus (white bars) and the PER.C6-passaged virus (gray bars) could infect the PER.C6-alpha2,6 ST cells very efficiently (right panel), whereas PER.C6 cells (left panel) were not very susceptible to infection by the primary clinical isolate. This shows that cells that over-express the alpha2,6 sialyltransferase are particularly useful to propagate primary virus isolates and shows that these cells are extremely useful in rapid and safe methods for the production of vaccines against, for instance, influenza infection.

Example 8

Titration of Influenza Virus Particles using PER.C6 Cells in FACS

A novel FACS-based method was employed to measure the titer of influenza virus in supernatants. The procedure entails the quantification of replication-competent virions by detecting the fraction of cells that are productively infected within the first round of viral replication. Using a suspension culture of PER.C6 and a moiety of infection between 0.01 and 1, it is possible to obtain very accurate values within a few hours. The same titration by plaque assay with MDCK cells, which is at the moment the standard assay for influenza virus titration used by many in the art, is much more lengthy (generally almost two weeks), labor demanding, and especially less reproducible. What follows is the technical description of the materials and method employed. Here, it is shown that suspension cells can be used for titration of influenza virus particles in supernatants using FACS analysis.

PER.C6 cells that were grown in suspension in serum-free AEM Medium (Gibco) were plated in a 24-well plate (1 ml cells per well at $1 \times 10^6$ cells/ml). Trypsin-EDTA (Gibco) was added to a final concentration of 3 µg/ml. Cells were infected with an influenza virus type A supernatant (X-127, a reassortant of A/Beijing/262/95 and X-31 (obtained from the National Institute for Biological Standards and Control). 200 µl virus supernatant were added to the cells in 3-fold dilution steps, starting with undiluted virus stock. A control of mock-infected cells was included. Following addition of the virus, cells were kept for 5 h at 35° C.

Infected cells were sampled (350 µl each) in 1.5 ml eppendorf tubes. Cold PBS was added up to 1 ml and the tubes were centrifuged for 5 min at 5,000 rpm in eppendorf bench centrifuge. Supernatant was discarded and cells were resuspended gently in 100 µl cold Cytoperm/Cytofix permeabilizing solution (Pharmingen). After 20 min at 4° C., cold PBS (900 µl) was added and cells pelleted again, as above. Pelleted cells were resuspended in 350 µl cold-staining medium (PBS, 1% BSA, 0.1% Na Azide) containing 5 µl of influenza A nucleoprotein-specific antibody labeled with FITC (Imagen Kit, Dako). Cells were incubated at 4° C. for 15 min to 30 min and subsequently washed once with 1 ml cold PBS and once with 1 ml 1× Cellfix fixing solution (Becton Dickinson). Cells were then analyzed by FACS or stored at 4° C. in the dark for up to 1 week for subsequent FACS analysis.

Figure 7:
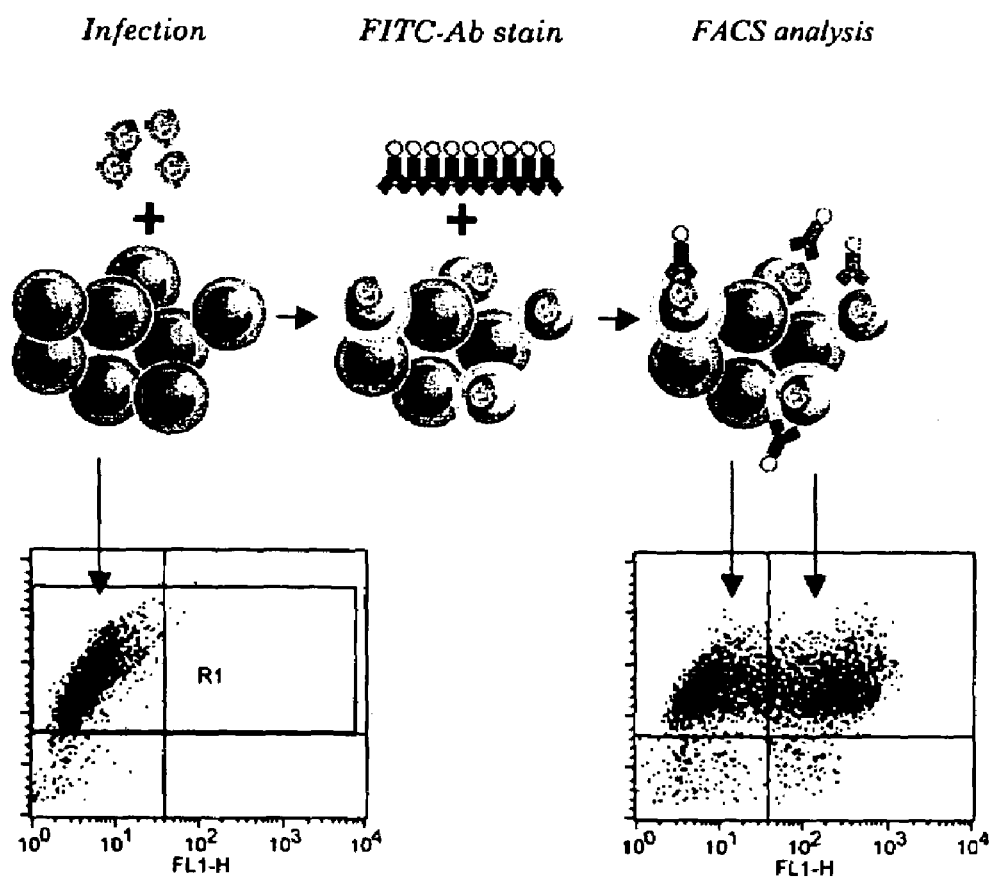
FIG. 7. Schematic representation of the influenza titration assay. First cells are infected with virus particles, then cells are incubated with antisera and subsequently used in FACS analysis in which infected cells can be separated and counted in the entire population of cells.

Stained cells were analyzed on a FACsort apparatus (Becton Dickinson). Influenza/FITC positive cells were detected in the FL1 channel and appeared in the upper right quadrant (FIG. 7). In the lower portion of the figure are plotted the results of the FACS analysis on uninfected cells and cells at 5 h post infection. The upper right quadrant and the upper left quadrant of the graphs represent the FITC-positive/infected and FITC-negative/uninfected cells, respectively.

Figure 8:
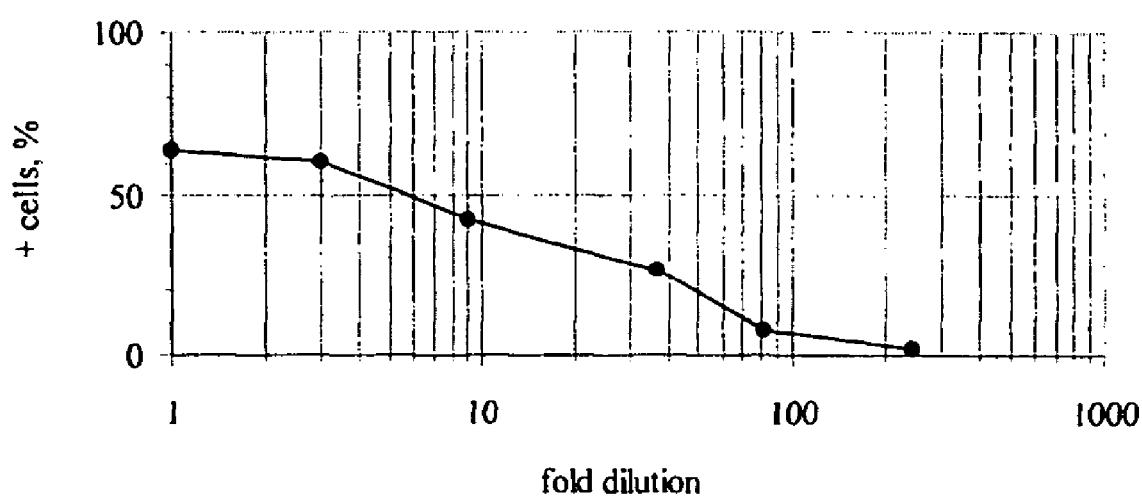
FIG. 8. Plot of the fraction of infected cells (%) over the dilution factor.

Infected cells were then plotted as percentage on the Y-axis over the dilution of the supernatant used to infect them on the X-axis (FIG. 8). The value that corresponds to 50% of infected cells represents the $TCID_{50}$ of the supernatant. Knowing that 1,000,000 cells were used for this initial infection, one derives that 200 μl supernatant diluted 1/6 contain 500,000 infectious particles, corresponding to a titer of $1.5 \times 10^7$ infectious particles/ml. When the same supernatant was quantified on the standard plaque assay with MDCK cells using standard procedures well known to persons skilled in the art, a value of $1.7 \times 10^7$ was obtained, with a variation of +/−50%.

It is obvious to one skilled in the art that different volumes and dilutions of virus supernatant can be used together with different amounts of PER.C6 to vary the sensitivity of the assay. Analogously, titers of influenza viruses other than X-127 can be measured, provided the appropriate antibody is used in the staining.

REFERENCES

Baum L G and Paulson J C (1990) Sialyloligosaccharides of the respiratory epithelium in the selection of human influenza virus receptor specificity. Acta Histochem Suppl 40:35-8

Claas E C, Osterhaus A D, van Beek R, De Jong J C, Rimmelzwaan G F, Senne D A, Krauss S, Shortridge K F and Webster R G (1998) Human influenza A H5N1 virus related to a highly pathogenic avian influenza virus. Lancet 351:472-427

Couceiro J N, Paulson J C and Baum L G (1993) Influenza virus strains selectively recognize sialyl-oligosaccharides on human respiratory epithelium; the role of the host cell in selection of hemagglutinin receptor specificity. Virus Res 29:155-165

Daniels P S, Jeffries S, Yates P, Schild G C, Rogers G N, Paulson J C, Wharton S A, Douglas A R, Skehel J J and Wiley D C (1987) The receptor-binding and membrane-fusion properties of influenza virus variants selected using anti-haemagglutinin monoclonal antibodies. Embo J 6:1459-1465

Gambaryan A S, Robertson J S and Matrosovich M N (1999) Effects of egg-adaptation on the receptor-binding properties of human influenza A and B viruses. Virology 258:232-239

Gambaryan A S, Tuzikov A B, Piskarev V E, Yamnikova S S, Lvov D K, Robertson J S, Bovin N V and Matrosovich M N (1997) Specification of receptor-binding phenotypes of influenza virus isolates from different hosts using synthetic sialylglycopolymers: non-egg-adapted human H1 and H3 influenza A and influenza B viruses share a common high binding affinity for 6'-sialyl (N-acetyllactosamine). Virology 232:345-350

Gibbs M J, Armstrong J S and Gibbs A J (2001) Recombination in the hemagglutinin gene of the 1918 "Spanish flu." Science 293:1842-1845

Govorkova E A, Matrosovich M N, Tuzikov A B et al. (1999) Selection of receptor-binding variants of human influenza A and B viruses in baby hamster kidney cells. Virology 262:31-38

Hatta N, Gao P, Halfmann P and Kawaoka Y (2001) Molecular basis for high virulence of Hong Kong H5N1 influenza A viruses. Science 293:1840-1842

Ilobi C P, Henfrey R, Robertson J S, Mumford J A, Erasmus B J and Wood J M (1994) Antigenic and molecular characterization of host cell-mediated variants of equine H3N8 influenza viruses. J Gen Virol 75:669-673

Ito T, Suzuki Y, Takada A, Kawamoto A, Otsuki K, Masuda H, Yamada M, Suzuki T, Kida H and Kawaoka Y (1997) Differences in sialic acid-galactose linkages in the chicken egg amnion and allantois influence human influenza virus receptor specificity and variant selection. J Virol 71:3357-3362

Liu C K, Wei G, Atwood W J (1998) Infection of glial cells by the human polyomavirus JC is mediated by an N-linked glycoprotein containing terminal alpha(2-6)-linked sialic acids. J Virol 72:4643-4639

Newman R W, Jennings R, Major D L, Robertson J S, Jenkins R, Potter C W, Burnett I, Jewes L, Anders M, Jackson D and et al. (1993) Immune response of human volunteers and animals to vaccination with egg-grown influenza A (H1N1) virus is influenced by three amino acid substitutions in the haemagglutinin molecule. Vaccine 11:400-406

Pau M G, Ophorst C, Koldijk M H, Schouten G, Mehtali M and Uytdehaag F (2001) The human cell line PER.C6 provides a new manufacturing system for the production of influenza vaccines. Vaccine 19:2716-2721

Potter W P (1998). Chronicle of influenza pandemics. In Textbook of influenza, NKG, R G Webster and A J Hay, eds. (Oxford) pp. 3-18

Robertson J S, Cook P, Nicolson C, Newman R and Wood J M (1994) Mixed populations in influenza virus vaccine strains. Vaccine 12:1317-1322.

Rogers G N, Daniels R S, Skehel J J, Wiley D C, Wang X F, Higa H H and Paulson J C (1985) Host-mediated selection of influenza virus receptor variants. Sialic acid-alpha 2,6Gal-specific clones of A/duck/Ukraine/1/63 revert to sialic acid-alpha 2,3Gal-specific wild type in ovo. J Biol Chem 260:7362-7367

Subbarao K, Klimov A, Katz J, Regnery H, Lim W, Hall H, Perdue M, Swayne D, Bender C, Huang J, Hemphill M, Rowe T, Shaw M, Xu X, Fukuda K and Cox N (1998) Characterization of an avian influenza A (H5N1) virus isolated from a child with a fatal respiratory illness. Science 279:393-396

Suzuki Y (1994) Gangliosides as influenza virus receptors. Variation of influenza viruses and their recognition of the receptor sialo-sugar chains. Prog Lipid Res 33:429-457

Suzuki Y, Kato H, Naeve C W and Webster R G (1989) Single-amino-acid substitution in an antigenic site of influenza virus hemagglutinin can alter the specificity of binding to cell membrane-associated gangliosides. J Virol 63:4298-4302

Suzuki T, Portner A, Scroggs R A, Uchikawa M, Koyama N, Matsuo K, Suzuki Y and Takimoto T (2001) Receptor specificities of human respiroviruses. J Virol 75:4604-4613

Walters R W, Yi S M, Keshavjee S, Brown K E, Welsh M J, Chiorini J A and Zabner J (2001) Binding of adeno-associated virus type 5 to 2,3-linked sialic acid is required for gene transfer. J Biol Chem 276:20610-20616

What is claimed is:

1. A method for producing an influenza virus particle, said method comprising the steps of:
   contacting a human embryonal retina cell transformed with E1 of an adenovirus with an influenza virus particle in a culture medium under conditions conducive to infection of said cell by said influenza virus particle, wherein the influenza virus particle is from an influenza isolate obtained from a subject infected with influenza virus; and
   culturing said cell under conditions conducive to propagation of said influenza virus particle, wherein said cell comprises a heterologous nucleic acid encoding an alpha2,6 sialyltransferase or a functional equivalent thereof and overexpresses the alpha2,6 sialyltransferase or functional equivalent thereof as compared to the cell that does not comprise the heterologous nucleic acid.

2. A method for producing an influenza virus particle, the method comprising:
   providing a host cell that is a human embryonal retina cell transformed with E1 of an adenovirus;
   expressing a nucleic acid encoding alpha2,6 sialyltransferase in the host cell by a heterologous nucleic acid at a higher level than the expression of alpha2,6 sialyltransferase in a cell the same as the host cell, but not comprising the heterologous nucleic acid;
   infecting the host cell with an influenza virus particle from an influenza isolate obtained from a subject infected with influenza virus, and
   culturing the host cell under conditions that allow for propagation of the influenza virus particle.

3. The method according to claim 2, comprising overexpressing a human alpha2,6 sialyltransferase.

4. The method according to claim 2, wherein the influenza isolate is obtained from at least one influenza-infected mammal.

5. The method according to claim 4, wherein the influenza isolate is obtained from a human or a pig.

6. The method according to claim 2, wherein the influenza isolate is obtained from at least one bird.

7. The method according to claim 2, wherein the host cell is a PER.C6 cell wherein the heterologous nucleic acid has been introduced.

8. The method according to claim 2, wherein the heterologous nucleic acid is integrated into a genome of the host cell.

9. The method according to claim 2, said method further comprising making a vaccine by inactivating the propagated influenza virus particles.

10. The method according to claim 9, further comprising: treating the inactivated influenza virus particles to yield antigenic parts; and isolating at least one antigenic part.

11. The method according to claim 10, comprising isolating at least one antigenic part of a hemagglutinin or neuraminidase protein, or combinations thereof, from an influenza virus.

* * * * *

SEQUENCE LISTING

<160> NUMBER OF SEQ ID NOS: 4

<210> SEQ ID NO 1
<211> LENGTH: 39
<212> TYPE: DNA
<213> ORGANISM: Artificial
<220> FEATURE:
<223> OTHER INFORMATION: Forward primer for human alpha2,6
      sialyltransferase

<400> SEQUENCE: 1 tttttggat ccatgattca caccaacctg aagaaaaag                              39

<210> SEQ ID NO 2
<211> LENGTH: 35
<212> TYPE: DNA
<213> ORGANISM: Artificial
<220> FEATURE:
<223> OTHER INFORMATION: Reverse primer for human alpha2,6
      sialyltransferase

<400> SEQUENCE: 2
ttttttctta agttagcagt gaatggtccg gaagc                                 35

<210> SEQ ID NO 3
<211> LENGTH: 36
<212> TYPE: DNA
<213> ORGANISM: Artificial
<220> FEATURE:
<223> OTHER INFORMATION: Forward primer for human alpha2,3
      sialyltransferase

<400> SEQUENCE: 3 tttttggat ccatgtgtcc tgcaggctgg aagctc                                 36

<210> SEQ ID NO 4
<211> LENGTH: 38
<212> TYPE: DNA
<213> ORGANISM: Artificial
<220> FEATURE:
<223> OTHER INFORMATION: Reverse primer for human alpha2,3
      sialyltransferase

<400> SEQUENCE: 4
ttttttctta agtcagaagg acgtgaggtt cttgatag                              38